United States Patent
Zhu et al.

(10) Patent No.: US 10,463,745 B2
(45) Date of Patent: Nov. 5, 2019

(54) MATERIALS FOR TISSUE REGENERATION

(71) Applicant: Northwestern University, Evanston, IL (US)

(72) Inventors: Yunxiao Zhu, Evanston, IL (US); Zdravka Cankova, Evanston, IL (US); Milan Mrksich, Evanston, IL (US); Guillermo A. Ameer, Chicao, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/573,166

(22) PCT Filed: May 12, 2016

(86) PCT No.: PCT/US2016/031993
§ 371 (c)(1),
(2) Date: Nov. 10, 2017

(87) PCT Pub. No.: WO2016/183277
PCT Pub. Date: Nov. 17, 2016

(65) Prior Publication Data
US 2018/0125990 A1    May 10, 2018

Related U.S. Application Data

(60) Provisional application No. 62/160,334, filed on May 12, 2015.

(51) Int. Cl.
| A61K 47/58 | (2017.01) |
| A61K 38/39 | (2006.01) |
| A61L 26/00 | (2006.01) |
| A61K 47/59 | (2017.01) |

(52) U.S. Cl.
CPC .............. *A61K 47/58* (2017.08); *A61K 38/39* (2013.01); *A61K 47/585* (2017.08); *A61K 47/593* (2017.08); *A61L 26/008* (2013.01); *A61L 26/0014* (2013.01); *A61L 26/0066* (2013.01); *A61L 2300/252* (2013.01); *A61L 2300/412* (2013.01); *A61L 2430/00* (2013.01)

(58) Field of Classification Search
CPC ................................. A61K 47/58; A61K 38/39
See application file for complete search history.

(56) References Cited

U.S. PATENT DOCUMENTS

| | | |
|---|---|---|
| 3,779,242 A | 12/1973 | McCullough |
| 4,399,816 A | 8/1983 | Spangler |
| 4,709,695 A | 12/1987 | Kohn et al. |
| 4,732,146 A | 3/1988 | Fasline et al. |
| 4,907,579 A | 3/1990 | Kum |
| 4,909,243 A | 3/1990 | Frank et al. |
| 4,917,112 A | 4/1990 | Kalt |
| 4,926,883 A | 5/1990 | Strock |
| 5,086,763 A | 2/1992 | Hathman |
| 5,167,613 A | 12/1992 | Karami et al. |
| 6,194,378 B1 | 2/2001 | Clark et al. |
| 6,933,280 B2* | 8/2005 | Castillo .................. C07K 14/78 424/184.1 |
| 7,189,698 B2* | 3/2007 | Castillo .................. C07K 14/78 424/184.1 |
| 7,189,699 B2* | 3/2007 | Castillo .................. C07K 14/78 424/184.1 |
| 7,208,475 B2* | 4/2007 | Castillo .................. C07K 14/78 424/184.1 |
| 7,229,968 B2* | 6/2007 | Castillo .................. C07K 14/78 424/184.1 |
| 7,276,483 B1* | 10/2007 | Castillo .................. A61K 38/10 424/184.1 |
| 7,384,910 B2* | 6/2008 | Castillo .................. A61K 38/08 514/17.8 |
| 7,517,654 B2 | 4/2009 | Min |
| 7,759,311 B2* | 7/2010 | Castillo .................. A61K 38/08 514/21.7 |
| 8,003,612 B2* | 8/2011 | Lake ...................... A61K 38/08 514/17.8 |
| 8,193,145 B2 | 6/2012 | Burkin et al. |
| 8,404,264 B2 | 3/2013 | Ameer et al. |
| 8,568,765 B2 | 10/2013 | Ameer et al. |
| 8,580,912 B2 | 11/2013 | Ameer et al. |
| 8,758,796 B2 | 6/2014 | Ameer et al. |
| 8,772,437 B2 | 7/2014 | Ameer et al. |
| 8,911,720 B2 | 12/2014 | Ameer et al. |
| 9,289,500 B2* | 3/2016 | Guan ...................... A61K 47/42 |
| 2003/0013648 A1* | 1/2003 | Castillo .................. C07K 14/78 514/1.1 |

(Continued)

FOREIGN PATENT DOCUMENTS

WO    WO 2011050342 A2    4/2011

OTHER PUBLICATIONS

Fahmy et al., 2012, Novel Antimicrobial Organic Thermal Stabilizer and Co-Stabilizer for Rigid PVC, Molecules, 17: 7927-7940.*
Yang et al., 2014, A Thermoresponsive Biodegradable Polymer with Intrinsic Antioxidant Properties, Biomacromolecules, 15: 3942-3952.*
Allmendinger et al., Fluoroolefin dipeptide isosteres-II.: Enantioselectlve synthesis of both antipodes of the phe-gly dlpeptide mimic. Tetrahedron Letters. 1990; 31(50):7301-7304.
Apikoglu et al., Effect of topical insulin on cutaneous wound healing in rats with or without acute diabetes. Clin Exp Dermatol. 2010; 35(2):180-185.
Arshady, Preparation of biodegradable microspheres and microcapsules: 2. Polyactides and related polyesters. J Controlled Release. 1991; 17(1):1-21.

(Continued)

*Primary Examiner* — Amber D Steele
(74) *Attorney, Agent, or Firm* — Casimir Jones SC; David W. Staple

(57) ABSTRACT

Provided herein are materials for the promotion of tissue regeneration, and methods of promoting tissue regeneration and wound healing therewith. In particular, materials displaying laminin-derived peptide sequences that facilitate cell migration into the material, and methods of use thereof, are provided.

7 Claims, 11 Drawing Sheets

Specification includes a Sequence Listing.

(56) References Cited

U.S. PATENT DOCUMENTS

| | | | |
|---|---|---|---|
| 2003/0118692 A1 | 6/2003 | Wang et al. | |
| 2005/0059602 A1* | 3/2005 | Castillo | C07K 14/78 514/1.1 |
| 2005/0153895 A1* | 7/2005 | Castillo | C07K 14/78 514/1.1 |
| 2005/0153896 A1* | 7/2005 | Castillo | C07K 14/78 514/1.1 |
| 2005/0153897 A1* | 7/2005 | Castillo | C07K 14/78 514/1.1 |
| 2005/0153898 A1* | 7/2005 | Castillo | C07K 14/78 514/17.8 |
| 2005/0244334 A1* | 11/2005 | Castillo | A61K 38/08 424/1.69 |
| 2008/0227721 A1* | 9/2008 | Castillo | A61K 38/08 514/1.1 |
| 2009/0253637 A1* | 10/2009 | Lake | A61K 38/08 514/1.1 |
| 2012/0207720 A1* | 8/2012 | Burkin | A61K 38/39 424/93.7 |
| 2013/0211500 A1 | 8/2013 | Kibbe et al. | |
| 2014/0037588 A1 | 2/2014 | Yang et al. | |
| 2014/0058049 A1 | 2/2014 | Ameer et al. | |
| 2014/0135407 A1 | 5/2014 | Ameer et al. | |
| 2014/0155516 A1 | 6/2014 | Ameer et al. | |
| 2014/0242123 A1* | 8/2014 | Guan | A61K 47/42 424/400 |
| 2014/0288002 A1* | 9/2014 | Panitch | C07K 9/00 514/17.1 |

OTHER PUBLICATIONS

Bagi et al., PPARγ activation, by reducing oxidative stress, increases NO bioavailability in coronary arterioles of mice with Type 2 diabetes, Am J Physiol Heart Circ Physiol, 2004; vol. 286(2), pp. H742-H748.
Banerjee et al., Wound healing activity of a collagen-derived cryptic peptide, Amino Acids. 2015; vol. 47(2), pp. 317-328.
Bellas et al., In vitro 3D full thickness skin equivalent tissue model using silk and collagen biomaterials, Macromol Biosci. 2012; vol. 12(12), pp. 1627-1636.
CDC, National diabetes fact sheet: national estimates and general information on diabetes and prediabetes in the United States, 12 pages, 2011.
Chorev et al., A dozen years of retro-inverso peptidomimetics. Acc Chem Res. 1993; 26(5):266-273.
Cortes et al., The Platelet Integrin αIIbβ3 Binds to the RGD and AGD Motifs in Fibrinogen, Chem Biol. 2009; vol. 16(9), pp. 990-1000.
Del Gaudio et al., Evaluation of in situ injectable hydrogels as controlled release device for ANXA1 derived peptide in wound healing, Carbohydrate Polymers. 2015; vol. 115(22), pp. 629-635.
Frank et al., Laminin 5 deposition regulates keratinocyte polarization and persistent migration. 2004; J Cell Sci, vol. 117, pp. 1351-1363.
Fujisaki et al., Keratinocyte apoptosis on type I collagen gel caused by lack of laminin May 10, 2011 deposition and Akt signaling. Exp Cell Res. 2002; 280(2):255-269.
Galiano et al., Quantitative and reproducible murine model of excisional wound healing. Wound Repair Regen. 2004; 12(4):485-492.
Galiano et al., Topical Vascular Endothelial Growth Factor Accelerates Diabetic Wound Healing through Increased Angiogenesis and by Mobilizing and Recruiting Bone Marrow-Derived Cells, Am J Pathol. 2004; vol. 164(4), pp. 1935-1947.
Gallagher et al., Diabetic impairments in NO-mediated endothelial progenitor cell mobilization and homing are reversed by hyperoxia and SDF-1a, J Clin Invest. 2007; vol. 117(5), pp. 1249-1259.
Gibran et al., Diminished Neuropeptide Levels Contribute to the Impaired Cutaneous Healing Response Associated with Diabetes Mellitus. J Surg Res. 2002; 108(1):122-128.

Goldfinger et al., The alpha3 laminin subunit, alpha6beta4 and alpha3beta1 integrin coordinately regulate wound healing in cultured epithelial cells and in the skin, J Cell Sci. 1999; vol. 112, pp. 2615-2629.
Gong et al., A biodegradable hydrogel system containing curcumin encapsulated in micelles for cutaneous wound healing, Biomaterials. 2013; vol. 34(27), pp. 6377-6387.
Gonzales et al., A Cell Signal Pathway Involving Laminin-5, α3β1 Integrin, and Mitogen-activated Protein Kinase Can Regulate Epithelial Cell Proliferation, Mol Biol Cell. 1999; vol. 10(2), pp. 259-270.
Greenhalg, Wound healing and diabetes mellitus, Clin Plastic Surg. 2003; vol. 30, pp. 37-45.
Hamed et al., Topical Erythropoietin Promotes Wound Repair in Diabetic Rats. J Invest Dermatol. 2010; 130(1):287-294.
Hoffman et al., The Stereoselective Synthesis of 2-Alkyl .gamma.-Keto Acid and Heterocyclic Ketomethylene Peptide Isostere Core Units Using Chiral Alkylation by 2-Triflyloxy Esters. J Org Chem. 1995; 60(16):5107-5113.
Holland et al., Polymers for biodegradable medical devices. 1. The potential of polyesters as controlled macromolecular release systems. J Controlled Release. 1986; 4(3):155-180.
Hozumi et al., Chain-Specific Heparin-Binding Sequences in the Laminin α Chain LG45 Modules, Biochemisty. 2009; vol. 48(23), pp. 5375-5381.
Humphries et al., Integrin ligands at a glance. 2006; vol. 119, pp. 3901-3903.
Illum, L., et al. (eds.) Polymers in Controlled Drug Delivery. Wright, Bristol, 1987.
International Search Report of related PCT/US2016/031993, dated Aug. 22, 2016, 11 pages.
Katagiri et al., Screening of integrin-binding peptides from the laminin α4 and α5 chain G domain peptide library, Archives of Biochemistry and Biophysics. 2012; vol. 521, pp. 32-42.
Kolokol'Chikova et al., Morphological Changes in Burn Wounds after Transplantation of Allogenic Fibroblasts. Bull Exp Biol Med. 2001; 131(1):89-93.
Lavielle et al., Importance of the leucine side-chain to the spasmogenic activity and binding of Substance P analogues. Int J Peptide Protein Res. 1993; 42.
Li et al., In situ injectable nano-composite hydrogel composed of curcumin, N,O-carboxymethyl chitosan and oxidized alginate for wound healing application. Int J Pharm. 2012; 437:110-119.
Li et al., Research of PDGF-BB Gel on the Wound Healing of Diabetic Rats and Its Pharmacodynamics. J Surg Res. 2008; 145(1):41-48.
Lin et al., Laminin α5 Chain Adhesion and Signaling in Conjunctival Epithelial Cells, Invest Opthamol Vis Sci, vol. 43(8), 2615-2621, 2002.
Liu et al., A short peptide from frog skin accelerates diabetic wound healing, FEBS Journal, vol. 281(20), pp. 4633-4643, 2014.
Livant et al., The PHSRN sequence induces extracellular matrix invasion and accelerates wound healing in obese diabetic mice, J Clin Invest, vol. 105(11), pp. 1537-1545, 2000.
Luisi et al., φ(SO2-NH) transition state isosteres of peptides. Synthesis of the glutathione disulfide analogue. Tetrahedron Lett. 2003; 34(14):2391-2392.
Maleej et al., Rhelogical, dermal wound healing and in vitro antioxidant properties of exopolysaccharide hydrogel from Pseudomonas stutzeri AS22. Colloids Surfaces B Biointerfaces. 2014; 123:814-824.
Margareta et al., Friends or foes—bipolar effects of the tumour stroma in cancer. Nat Rev Cancer. 2004; 4:839-849.
Michaels et al., db/db mice exhibit severe wound-healing impairments compared with other murine diabetic strains in a silicone-splinted excisional wound model. Wound Repair Regen. 2007; 15(5):665-670.
Moura et al., Chitosan-based dressings loaded with neurotensin—an efficient strategy to improve early diabetic wound healing. Acta Biomaterialia. 2014; 10(2):843-857.
Moura et al., Recent advances on the development of wound dressings for diabetic foot ulcer treatment—A review. Acta Biomaterialia. 2013; 9(7):7093-7114.

(56) References Cited

OTHER PUBLICATIONS

Murphy et al., Substrates for Cell Adhesion Prepared via Active Site-Directed Immobilization of a Protein Domain, Langmuir, vol. 20(4), pp. 1026-1030, 2004.
Nguyen et al., Deposition of Laminin 5 by Keratinocytes Regulates Integrin Adhesion and Signaling, J Biol Chem. 2000; vol. 275, pp. 31896-31907.
Nielsen et al., Identification of a Major Heparin and Cell Binding Site in the LG4 Module of the Laminin α5 Chain, J Biol Chem. 2000; vol. 275, pp. 14517-41523.
Ostresh et al., "Libraries from libraries": chemical transformation of combinatorial libraries to extend the range and repertoire of chemical diversity, PNAS USA. 1994; vol. 91(23), pp. 11138-11142.
Park et al., Importance of defining experimental conditions in a mouse excisional wound model. Wound Repair Regen. 2015; 23(2):251-261.
Philp et al., Thymosin β4 and a synthetic peptide containing its actin-binding domain promote dermal wound repair in db/db diabetic mice and in aged mice. Wound Repair Regen. 2003; 11(1):19-24.
Pitt C. G., The controlled parenteral delivery of polypeptides and proteins. Int J Phar. 1990; 59(3):173-196.
Price et al., The Role of Allogenic Fibroblasts in an Acute Wound Healing Model. Plast Reconstr Surg. 2004; 113(6):1719-1729.
Raja et al., In vitro and in vivo assessments of a 3-(3,4-dihydroxyphenyl)-2-propenoic acid bioconjugated gelatin-based injectable hydrogel for biomedical applications, J Mater Chem B. 2015; 00:1-15.
Rizzi et al., Recent advances in dermal wound healing: biomedical device approaches. Expert Rev Med Devices. 2010; 7(1):143-154.
Rodgers et al., Histological evaluation of the effects of angiotensin peptides on wound repair in diabetic mice. Exp Dermatol. 2003; 12(6):789-790.
Rousselle et al., The syndecan binding sequence KKLRIKSKEK in laminin α3 LG4 domain promotes epidermal repair. Eur J Dermatol. 2013; pp. 1-9.
Roy et al., Fibronectin Matrix Mimetics Promote Full-Thickness Wound Repair in Diabetic Mice, Tissue Eng Part A. 2013; vol. 19, pp. 2517-2526.
Sasaki et al., Protection of φ(CH2NH) Peptide Bond with 2,4-Dimethoxybenzyl Group in Solid-Phase Peptide Synthesis, Chem Pharm Bull. 1997; vol. 45(1), pp. 13-17.
Schafer et al., Cancer as an overhealing wound: an old hypothesis revisited, Nat Rev Mol Cell Biol. 2008; vol. 9(8), pp. 628-638.
Schmidt et al., Structure-activity relationships of dermorphin analogues containing N-substituted amino acids in the 2-position of the peptide sequence. Int J Peptide Protein Res. 1995; 46(1).
Scott et al., Topical Substance P Increases Inflammatory Cell Density in Genetically Diabetic Murine Wounds, Wound Repair Regen. 2008; vol. 16(4), pp. 529-533.
Seet et al., Shelf-Life Evaluation of Bilayered Human Skin Equivalent, MyDerm™, PloS One. 2012; vol. 7(8), pp. e40978.
Senyurek et al., Processing of Laminin α Chains Generates Peptides Involved in Wound Healing and Host Defense, J Innate Immmun. 2014; vol. 6, pp. 467-484.
Serrano et al., Novel Biodegradable Shape-Memory Elastomers with Drug-Releasing Capabilities. Adv Mater. 2011; 23(19):2211-2215.
Sherman et al., Compatibility of thioamides with reverse turn features: synthesis and conformational analysis of two model cyclic pseudopeptides containing thioamides as backbone modifications. J Am Chem Soc. 1990; 112(1):433-441.
Singh et al., Preventing Foot Ulcers in Patients With Diabetes, JAMA. 2005; vol. 293(2), pp. 217-228.
Spatola, Synthesis of Pseudopeptides. Methods Neurosci. 1993; 13:19-42.
Steed et al., Promotion and Acceleration of Diabetic Ulcer Healing by Arginine-Glycine-Aspartic Acid (Rgd) Peptide Matrix. Diabetes Care. 1995;18(1).
Strukova et al., Immobilized Thrombin Receptor Agonist Peptide Accelerates Wound Healing in Mice, Clin Appl Thromb Hemost. 2001; vol. 7(4), pp. 325-329.
Tran et al., In Situ Forming and Rutin-Releasing Chitosan Hydrogels As Injectable Dressings for Dermal Wound Healing, Biomacromolecules. 2011; vol. 12(8), pp. 2872-2880.
Van Der Veen et al., Biological background of dermal substitutes. Burns. 2010; 36(3):305-321.
Waldeck et al., Interpenetrating polymer networks containing gelatin modified with PEGylated RGD and soluble KGF: Synthesis, characterization, and application in in vivo critical dermal wound. J Biomed Mater Res Part A. 2007; 82A(4):861-871.
Werner et al., Induction of keratinocyte growth factor expression is reduced and delayed during wound healing in the genetically diabetic mouse, J Investig Dermatol. 1994; vol. 103(4), pp. 469-473.
Wong et al., Tissue engineering for the management of chronic wounds: current concepts and future perspectives, Exp Dermatol. 2012; vol. 21, pp. 729-734.
Xu et al., Extracellular matrix alters PDGF regulation of fibroblast integrins, J Cell Biol. 1996; vol. 132, pp. 239-249.
Yang et al., A Thermoresponsive Biodegradable Polymer with Intrinsic Antioxidant Properties, Biomacromolecules. 2014; vol. 15(11), pp. 3942-3952.
Yang et al., Synthesis and evaluation of poly(diol citrate) biodegradable elastomers, Biomaterials, 2006, 27(9), pp. 1889-1898.
Ziyadeh et al., A Matched Cohort Study of the Risk of Cancer in Users of Becaplermin. Adv Skin Wound Care. 2011; 24(1):31-39.

* cited by examiner

MATERIALS FOR TISSUE REGENERATION

CROSS REFERENCE TO RELATED APPLICATIONS

The present invention is a § 371 National Entry application of International Patent Application PCT/US2016/031993, filed May 12, 2016, which claims priority to U.S. Provisional Patent Application 62/160,334, filed May 12, 2015, each of which are incorporated by reference in its entirety.

FIELD

Provided are herein materials for the promotion of tissue regeneration, and methods of promoting tissue regeneration and wound healing therewith. In particular, materials displaying laminin-derived peptide sequences that facilitate cell migration into the material, and methods of use thereof, are provided.

BACKGROUND

Diabetic foot ulcers are the leading cause of non-traumatic limb amputations in the United States, with approximately 73,000 cases annually (ref 1; incorporated by reference in its entirety). Approximately 25% of diabetics are at risk of developing foot ulcers, which can lead to frequent hospitalizations due to severe impairment of the wound healing process (ref 2; incorporated by reference in its entirety). Although the field of wound care and management is well-established, the treatment of diabetic foot ulcers still remains a challenge (ref 3; incorporated by reference in its entirety). This discrepancy stems from the fact that traditional wound care fails to address the issues associated with the impaired wound healing process in diabetic patients.

To resolve this problem, most academic and industrial efforts have focused on the release of a drug or protein to pharmacologically affect the wound and improve healing rates (refs. 3-18; incorporated by reference in their entireties). Efforts have also used auto-/allogeneic cells to recellularize skin tissue equivalents (refs. 19-21; incorporated by reference in their entireties). Although with some promising data, there are substantial hurdles that a drug, protein releasing system and cell-based system must overcome from a regulatory standpoint, including dosing and the safety and efficiency studies, which lead to delayed development time and high costs. Frequent reapplication is often required due to lack of sustained release capabilities for many of the materials reported in the literature. Furthermore, there are often side effects that are only found with general patient use and can hinder the widespread use of the product as is the case with Regranex (becalpermin) which increases the risk of cancer (refs. 22-24; incorporated by reference in their entireties). Skin equivalents, on the other hand, normally end up being costly with limited shelf life due to incorporation of live cells (refs. 25, 26; incorporated by reference in their entireties). The transplanted cells with in those scaffolds also have been shown to have questionable survival rate on the wound bed according to several studies (ref 27, 28; incorporated by reference in their entireties). What is needed are materials and wound dressings that overcome these existing obstacles and address the issue of wound care, particularly for diabetic patients.

SUMMARY

Provided herein are materials for the promotion of tissue regeneration, and methods of promoting tissue regeneration and wound healing therewith. In particular, materials displaying laminin-derived peptide sequences that facilitate cell migration into the material, and methods of use thereof, are provided.

In some embodiments, provided herein are compositions comprising a carrier conjugated to laminin-based peptide that promotes cell adhesion, cell proliferation, and/or cell migration into the composition. In some embodiments, the laminin-based peptide is an A5G81-based peptide. In some embodiments, the A5G81-based peptide comprises at least 75% sequence similarity with SEQ ID NO: 1. In some embodiments, the A5G81-based peptide comprises a segment with at least 75% sequence similarity with SEQ ID NO: 1. In some embodiments, the carrier comprises a polyester, polyurethane, polycarbonate, polyanhydride, polyphosphoester, or a mixture thereof. In some embodiments, the carrier is a biocompatible and biodegradable polymer. In some embodiments, the polymer comprises a polyester. In some embodiments, polyester comprises a citric acid polyester. In some embodiments, the citric acid polyester comprises poly(polyethyleneglycol citrate-co-N-isopropylacrylamide) (PPCN). In some embodiments, the composition comprises a PPCN matrix conjugated to a peptide comprising a segment with at least 75% sequence similarity to SEQ ID NO: 1. In some embodiments, the peptide and/or the PPCN further comprise reactive groups for conjugation. In some embodiments, the peptide comprises a terminal cysteine for conjugation to the PPCN via a BMPH linker.

In some embodiments, provided herein are wound dressings comprising the compositions and materials described herein.

In some embodiments, provided herein is the use of a wound dressing comprising the compositions and materials described herein for the promotion of wound healing. In some embodiments, the wound is a diabetic ulcer.

In some embodiments, provided herein are methods comprising applying a wound dressing, composition, or material described herein to a wound for the promotion of wound healing. In some embodiments, the wound is a diabetic ulcer.

In some embodiments, provided herein are methods of promoting wound healing, comprising administering to a wound a thermoresponsive material comprising a polymer matrix displaying a A5G81-based peptides, wherein the thermoresponsive material is liquid at room temperature but forms a hydrogel upon application to the wound.

These embodiments and other embodiments within the scope herein are described in greater detail in the Detailed Description.

DEFINITIONS

Figure 1:
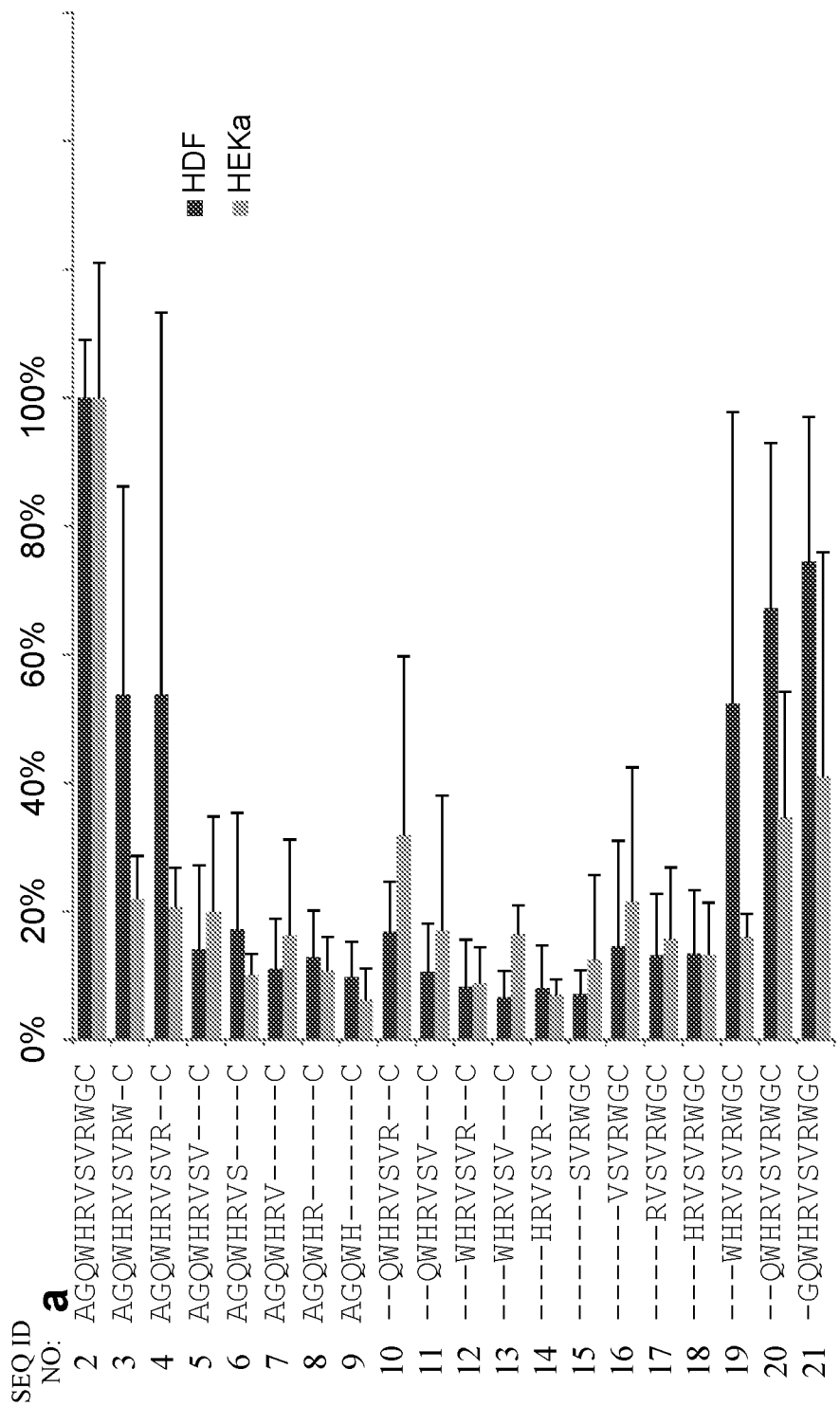
FIG. 1. Most amino acid residues significantly contribute to the bioactivity of A5G81. Adhesion of HDFs and HEKas significantly decreases on SAMs presenting (a) truncated versions of A5G81 and (b) A-substituted versions of A5G81 relative to control.
Figure 1:
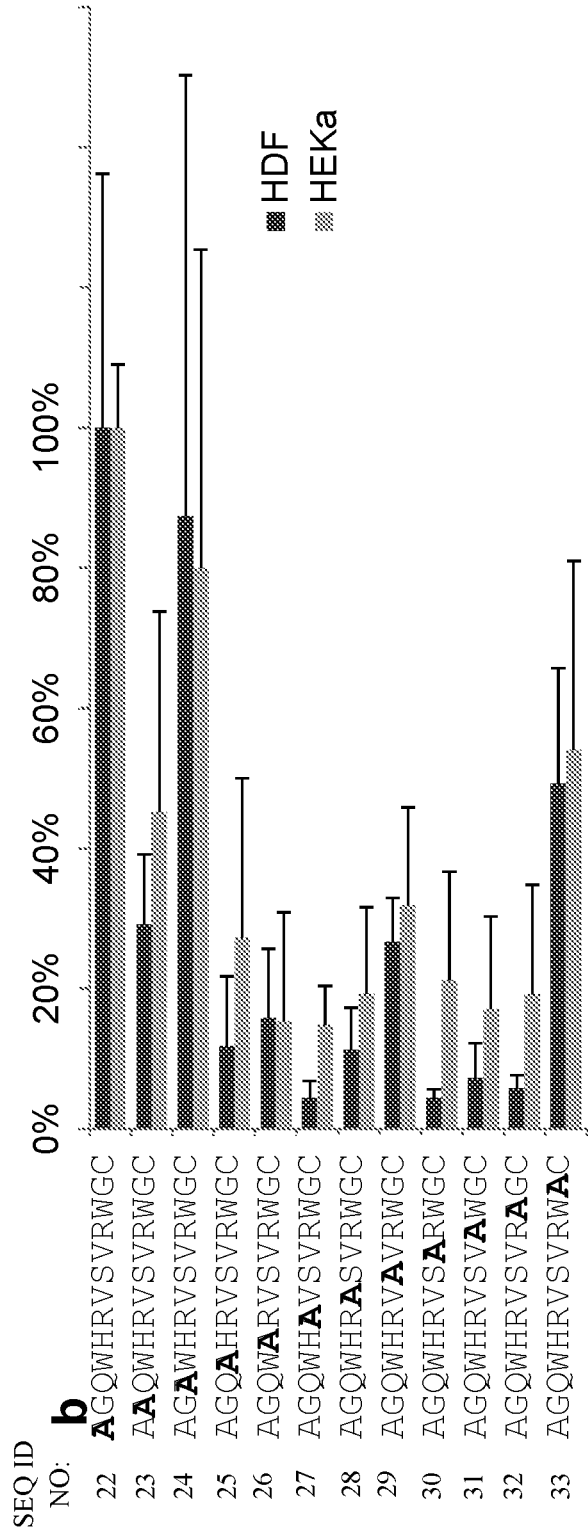

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "an A5G81-based peptide" is a reference to one or more A5G81-based peptides and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "polymer" refers to a chain of repeating structural units (e.g., citric acid, aliphatic diol, amino acids, etc.) or "monomers", typically of large molecular mass. Examples of polymers include homopolymers (single type of monomer subunits), copolymers (two types of monomer subunits), and heteropolymers (e.g., three or more types of monomer subunits). As used herein, the term "oligomer" refers to a polymer of only a few monomer units (e.g., 2, 3, 4, 5, or more) up to about 50 monomer units, for example a dimer, trimer, tetramer, pentamer, hexamer . . . decamer, etc.

As used herein, the term "linear polymer" refers to a polymer in which the molecules form long chains without branches or crosslinked structures.

As used herein, the term "branched polymer" refers to a polymer comprising a polymer backbone with one or more additional monomers, or chains of monomers, extending from polymer backbone. The degree of interconnectedness of the "branches" is insufficient to render the polymer insoluble.

As used herein, the terms "pre-polymer" refers to linear or branched polymers (e.g., soluble, not significantly crosslinked) that have the capacity to be crosslinked under appropriate conditions, but which have not yet been subjected to the appropriate conditions.

As used herein, the term "crosslinked polymer" refers to a polymer with a significant degree of interconnectedness between multiple polymer strands, the result of which is an insoluble polymer network (e.g., thermoset elastomer). For example, multiple polymer stands may be crosslinked to each other at points within their structures, not limited to the ends of the polymer chains.

As used herein, the term "hydrogel" refers to a three-dimensional (3D) crosslinked network of hydrophilic polymers that swells, rather than being dissolved, in water.

As used herein, the term "thermoresponsive" refers to materials that exhibit altered physical characteristics at different temperature ranges. Particularly relevant herein are "phase-transitioning thermoresponsive materials." Phase-transitioning thermoresponsive materials are soluble or in a liquid state at a first temperature range (e.g., below 26° C.) and insoluble or in a solid state at a second temperature range (e.g., 30-45° C.). A non-limiting example of a phase-transitioning thermoresponsive polymer is PPCN.

As used herein, the term "composite" refers to a material comprising two or more molecular, polymeric, and/or supra-molecular constituents that are miscible with one another, and may form a single homogeneous material. While covalent connections between the constituent components may be present, they are not required to form or maintain the composite or its homogeneity; rather, non-covalent and/or mechanical/physical interactions and associations are responsible for stabilizing the composite.

As used herein, the term "biocompatible" refers to materials and agents that are not toxic to cells or organisms. In some embodiments, a substance is considered to be "biocompatible" if its addition to cells in vitro results in less than or equal to approximately 10% cell death, usually less than 5%, more usually less than 1%, and preferably less than 0.1%.

The term "biodegradable," as used to describe the polymers, hydrogels, composites, and/or wound dressings herein, refers to compositions that are degraded or otherwise "broken down" under exposure to physiological conditions. In some embodiments, a biodegradable substance is a broken down by cellular machinery, enzymatic degradation, chemical processes, hydrolysis, etc. In some embodiments, a biodegradeable composition comprises hydrolyzable ester linkages.

As used herein, the phrase "physiological conditions" relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

As used herein, the term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers a short polymer of amino acids linked together by peptide bonds. In contrast to other amino acid polymers (e.g., proteins, polypeptides, etc.), peptides are of about 30 amino acids or fewer in length. A peptide may comprise natural amino acids, non-natural amino acids, amino acid analogs, and/or modified amino acids. A peptide may be a subsequence of naturally occurring protein or a non-natural (synthetic) sequence.

As used herein, the term "mutant peptide" refers to a variant of a peptide having a distinct amino acid sequence from the most common variant occurring in nature, referred to as the "wild-type" sequence. A mutant peptide may be a subsequence of a mutant protein or polypeptide (e.g., a subsequence of a naturally-occurring protein that is not the most common sequence in nature), or may be a peptide that is not a subsequence of a naturally occurring protein or polypeptide. For example, a "mutant laminin-based peptide" may be a subsequence of a mutant version of native laminin or may be distinct sequence not found in naturally-occurring laminin proteins.

As used herein, the term "synthetic peptide" refers to a peptide having a distinct amino acid sequence from those found in natural peptides and/or proteins. A synthetic peptide is not a subsequence of a naturally occurring protein, either the wild-type (i.e., most abundant) or mutant versions thereof. For example, a "synthetic laminin peptide" is not a subsequence of a naturally occurring laminin. A "synthetic peptide," as used herein, may be produced or synthesized by any suitable method (e.g., recombinant expression, chemical synthesis, enzymatic synthesis, etc.).

The terms "peptide mimetic" or "peptidomimetic" refer to a peptide-like molecule that emulates a sequence derived from a protein or peptide (e.g., A5G81). A peptide mimetic or peptidomimetic may contain amino acids and/or non-amino acid components. Examples of peptidomimitecs include chemically modified peptides, peptoids (side chains are appended to the nitrogen atom of the peptide backbone, rather than to the α-carbons), β-peptides (amino group bonded to the β carbon rather than the α carbon), etc.

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

"Non-conservative substitutions" involve the exchange of a member of one class for a member from another class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "substantially all," "substantially complete" and similar terms refer to greater than 99%; and the terms "substantially none," "substantially free of," and similar terms refer to less than 1%.

The term "about" allows for a degree of variability in a value or range. As used herein, the term "about" refers to values within 10% of the recited value or range (e.g., about 50 is the equivalent of 45-55).

DETAILED DESCRIPTION

Provided herein are materials for the promotion of tissue regeneration, and methods of promoting tissue regeneration and wound healing therewith. In particular, materials displaying laminin-derived peptide sequences that facilitate cell migration into the material, and methods of use thereof, are provided.

During development of embodiments herein, antioxidant/thermoresponsive/biodegradable, citric acid-based polymers that are functionalized with a laminin-derived peptide sequence were synthesized and evaluated; experiments demonstrate that these materials facilitate cell migration into the polymer. Material provide a hydrated environment, scavenges free radicals, and recruits specific cell populations without the use of soluble factors. Experiments conducted during development of embodiments herein demonstrated in a diabetic mouse model that peptide conjugation to the polymer accelerates wound closure. The use of this peptide-polymer therapy is extendable to other applications, such as bone regeneration, and other materials (e.g. lamin-based peptide conjugated to other polymers (e.g., with other properties/characteristics).

Experiments conducted during development of embodiments herein to synthesize and evaluate an antioxidant thermoresponsive biodegradable citric-based polymer functionalized with a novel laminin-derived α3β1 and α6β1 integrin binding peptide. The incorporation of this peptide not only facilitates human dermal fibroblasts cell spreading within such scaffold but also significantly increased the cell proliferation via an integrin-ligand binding dependent fashion. Experiments also showed that application of this polymer scaffold significantly accelerates wound closure in vivo with a splinted diabetic mice model, and provides a useful material for the treatment of, for example, diabetic ulcers.

Experiments conducted during development of embodiments herein demonstrate that functionalization with a laminin-derived cell binding peptide (e.g., A5G81), which facilitates cell binding via integrin receptors (e.g., into an antioxidant thermoresponsive hydrogel, into a polymeric scaffold, etc.) facilitates cell spreading and proliferation in vitro in 3D. Further, addition of the A5G81 adhesion sequence resulted in faster wound closure in diabetic mice as rapid granulation tissue formation and reepithelialization at early time points. These results demonstrate that materials displaying laminin-derived cell-binding peptides (e.g., A5G81) provide treatment for wounds (e.g., diabetic foot ulcers) without the need for additional soluble factors. Further, the demonstrated outperformance of A5G81 over RGD in the experiments herein demonstrate viable alternative cell binding peptides.

The exemplary peptide hydrogel used in experiments herein is based on a thermoresponsive biodegradable polymer poly(polyethyleneglycol co-citric acid-co-N isopropylacrylamide) (PPCN) (ref 29; incorporated by reference in its entirety). This material undergoes a rapid and reversible phase transition from liquid to solid at physiologically relevant temperatures to form a hydrogel with excellent water retention properties, and provides antioxidant activity including iron chelation, free radical scavenging and inhibition of lipid peroxidation (ref 29; incorporated by reference in its entirety). Such properties make PPCN an attractive material for use with the laminin-based peptides tested herein; however, the use of such laminin-based peptides with other materials (e.g., polymers, hydrogels, elastomers, etc.) is within the scope herein, based on the performance of the laminin-based peptides in the experiments conducted during development of embodiments herein.

In the examples provides herein, PPCN hydrogel was functionalized with either a laminin-derived peptide A5G81 or the commonly used fibronectin-derived peptide RGD (e.g., to allow improved cell interaction). Peptide conjugation was achieved through an exemplary click chemistry method using a bifunctional linker, chosen so that peptides with a terminal Cys residue are covalently bound to PPCN (e.g., other conjugation methods are within the cope herein). This method ensures that peptides are conjugated in a specific orientation, leaving peptide active sites fully accessible for cell-material interactions. The properties of the resulting materials include excellent water retention, injectability, and inhibition of lipid peroxidation. It was also found that addition of the A5G81 peptide significantly improved the human dermal fibroblasts cell proliferation with the scaffold through an integrin dependent manner which correlated well with observations of enhanced healing rate in the in vivo full-thickness diabetic wound model. Experiments conducted during development of embodiments herein demonstrate the use of the A5G81 adhesion peptide in the context of wound healing, and the results indicate that it is particularly suitable for this application as it outperformed the commonly used RGD adhesion sequence.

In some embodiments, compositions and materials described herein comprise a carrier (e.g., conjugated to a peptide component). In some embodiments, the carrier is a polymer, or a hydrogel thereof. In some embodiments, the carrier (e.g., conjugated to the peptide component) is any suitable wound dressing or material (e.g., a biodegradable wound dressing).

Suitable polymers that may find use in embodiments herein (e.g., in the formation of a hydrogel, crosslinked with another polymer, within a composite) include, but are not limited to: collagen, elastin, hyaluronic acid and derivatives, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), poly(diol citrate) (e.g., poly(octanediol citrate), etc.), casein, dextran and derivatives, polysaccharides, poly (caprolactone), fibrinogen, poly(hydroxyl acids), poly(L-lactide) poly(D,L lactide), poly(D,L-lactide-co-glycolide), poly(L-lactide-co-glycolide), copolymers of lactic acid and glycolic acid, copolymers of ε-caprolactone and lactide, copolymers of glycolide and ε-caprolactone, copolymers of lactide and 1,4-dioxane-2-one, polymers and copolymers that include one or more of the residue units of the monomers D-lactide, L-lactide, D,L-lactide, glycolide, ε-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly (hydroxyvaleric acid), polydioxanone, poly(ethylene terephthalate), poly(malic acid), poly(tartronic acid), polyanhydrides, polyphosphazenes, poly(amino acids), and copolymers of the above polymers as well as blends and combinations of the above polymers. (See generally, Illum, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986; herein incorporated by reference in their entireties).

In some embodiments, a polymer is selected from a polyester (e.g., poly (polyethyleneglycol citrate) acrylate, poly(polyethyleneglycol co-citric acid-co-N isopropylacrylamide), etc.), poly(diol citrate) (e.g., poly(butanediol citrate), poly(hexanediol citrate), poly(octanediol citrate), poly (decanediol citrate), poly(dodecanediol citrate), poly (hexadecanediol citrate), etc.), poly(hydroxyvalerate), poly (lactide-co-glycolide), poly(hydroxybutyrate), poly (hydroxybutyrate-co-valerate), polyorthoester, polyanhydride, poly(glycolic acid), poly(glycolide), poly(L-lactic acid), poly(L-lactide), poly(D,L-lactic acid), poly(D, L-lactide), poly(caprolactone), poly(trimethylene carbonate), polyester amide, or co-polymers or composites thereof.

In some embodiments, polymeric components comprise citric acid (e.g., a citric acid-based polymer/polyester). Citric acid is a reactive tricarboxylic acid that is part of the Krebs cycle and has been used as a key reactant monomer for the synthesis of polydiolcitrates with a wide range of properties and uses (Yang, J., et al., Synthesis and evaluation of poly(diol citrate) biodegradable elastomers. Biomaterials, 2006. 27(9): p. 1889-98.; U.S. Pat. Nos. 8,772,437; 8,758, 796; 8,580,912; 8,568,765; U.S. Pub. No. 2014/0155516; U.S. Pub. No. 2014/0135407; herein incorporated by reference in their entireties). Depending on the other monomers present in the citric acid polymer, materials are produced with controllable elasticity, biodegradability, thermoresponsiveness, and antioxidant properties (Serrano et al. Adv Mater, 2011. 23(19): p. 2211-5; Yang J., et al., A thermoresponsive biodegradable polymer with intrinsic antioxidant properties. Biomacromolecules, 2014. 15(11):3942-52; U.S. Pub. No. 2014/0037588; herein incorporated by reference in its entirety).

In some embodiments, a polymer is the polyesterification product of one or more acids (e.g., succinic acid, glutaric acid, adipic acid, pimelic acid, suberic acid, azelaic acid, sebacic acid, dodecanedioic acid, shorter or longer linear aliphatic diacids, citric acid, isocitric acid, aconitic acid, propane-1,2,3-tricarboxylic acid, trimesic acid, itaconic acid, maleic acid, etc.) and one or more diols or triols (e.g., polyethylene glycol, glycerol, linear aliphatic diol (e.g., butanediol, hexanediol, octanediol, decanediol, dodecanediol, and shorter or longer linear aliphatic diols), etc.). In some embodiments, a polymer is the polyesterification product of an acid (e.g., citric acid), polyethylene glycol, and one or more additional monomeric groups (e.g., glycerol 1,3-diglycerolate diacrylate, N-isoproylacrylamide monomer, etc.).

In some embodiments, any molecular entities capable of reacting with the reactive groups of, for example, citric acid, polyethylene glycol, or the other monomers and polymers described herein, may find use in the generation of polymeric compositions and networks thereof within the scope of the embodiments described herein. For example, additional monomer groups for use in embodiments herein include, but are not limited to: a lactide (e.g., D-lactide, L-lactide, or D,L-lactide), glycolide, lactone, carbonate, thiocarbonate, oxaketocycloalkane, thiooxaketocycloalkane, polyethylene glycol, glycerol, linear aliphatic diol (e.g., butanediol, hexanediol, octanediol, decanediol, dodecanediol, and shorter or longer linear aliphatic diols), linear aliphatic diacid (e.g., succinic acid, glutaric acid, adipic acid, pimelic acid, suberic acid, azelaic acid, sebacic acid, dodecanedioic acid, and shorter or longer linear aliphatic diacids), citric acid, isocitric acid, aconitic acid, propane-1,2,3-tricarboxylic acid, trimesic acid, diols, triols, polyols, itaconic acid, maleic acid, maleic anhydride, glycerol 1,3-diglycerolate diacrylate, glycerol dimethacrylate, 3-(acryloyloxy)-2-hydroxypropyl methacrylate, N-isopropylacrylamide, etc.

In some embodiments, a composition or composite herein comprises a polymer of citric acid, PEG, and glycerol 1,3-diglycerolate diacrylate (e.g., poly (polyethyleneglycol citrate) acrylate (PPCac), etc.). In some embodiments, a polymer comprises a polymer of citric acid, PEG, glycerol 1,3-diglycerolate diacrylate, and one or more additional monomers (e.g., N-isoproylacrylamide monomer, a diol or triol, etc.). In some embodiments, a polymer is the polymerization product of citric acid, PEG, and glycerol 1,3-diglycerolate diacrylate, and N-isoproylacrylamide monomer (e.g., poly(polyethyleneglycol citrate-co-N-isopropylacrylamide) (PPCN), etc.). In some embodiments, a polymer is the polymerization product of citric acid, PEG, and glycerol 1,3-diglycerolate diacrylate, and N-isoproylacrylamide monomer and one or more additional monomers (e.g., an acid, a diol or triol, etc.). In some embodiments, the polymer is poly(polyethyleneglycol citrate-co-N-isopropylacrylamide) (PPCN). In some embodiments, any of the aforementioned polymers are modified by the inclusion of additional monomers or substituents.

In some embodiments, a polymer comprises one or more linear aliphatic diols (butanediol, hexanediol, octanediol, decanediol, dodecanediol, or any linear aliphatic diol from about 2-20 carbons in length). In certain embodiments, the diol comprises one or more C2-C20 alkyl-diols, C2-C20 alkenyl-diols, or mixtures thereof. In certain other embodiments, the diol comprises one or more C2-C20 alkyl-diols, such as a C6-C20 alkyl-diol, or a C6-C14 alkyl-diol, or a C6-C12 alkyl-diol. For example, the diol can comprise an alkanediol, such as 1,12-dodecanediol, 1,10-decanediol, 1,8-octanediol, or a mixture thereof. In another example, the diol can comprise 1,10-decanediol, 1,8-octanediol, or a mixture thereof. In another example, the diol can comprise 1,8-octanediol (e.g., the polyester is poly(1,8-octanediol-citrate).

Polymers herein may be crosslinked, for example, by optionally including one or more hyperbranching monomers, such as a monomer comprising three alcohol functional groups (a "triol"), in order to control the degradation thereof. For example, glycerol can be added in addition to the citric acid and diol monomer (0-3 mol %, provided the molar ratio of carboxyl and hydroxyl group among the three monomers was maintained as 1/1). Glycerol is a hydrophilic component, and its addition can facilitate the water penetration into the network films which results in the faster degradation rate. Increasing amounts of glycerol can increase the break strength and Young's modulus of the resulting polyester. For example, the Young's modulus can range from 1 to 16 MPa, with strengths and strains at break of up to 10 MPa and 500%, respectively. Depending on the synthesis conditions, total degradation time may range from months to years.

In some embodiments, a polymer comprises additional substituents or functional groups appended to the polymer.

In some embodiments, reagents, monomer components of polymers, methods, reaction conditions, etc. that find use in embodiments described herein are described in: U.S. Pat. Nos. 8,911,720; 8,772,437; 8,758,796; 8,580,912; 8,568,765; 8,404,264; U.S. Pub. No. 2014/0058049; U.S. Pub. No. 2013/0211500; U.S. Prov. App. No. 62/160,334; herein incorporated by reference in their entireties.

In some embodiments, the polymeric component is a pre-polymer, linear polymer, branched polymer, crosslinked polymer, hydrogel, elastomer, etc.

In some embodiments, materials comprise a poly(glycerol-diacid). A poly(glycerol-diacid), as used herein, is a polyester which is prepared from a triol monomer, glycerol, and a second monomer comprising two carboxylic acid functional groups (a "diacid") according to methods familiar to one skilled in the art. For example, suitable poly(glycerol-diacid)s can be prepared as described in U.S. Patent Application Publication No. 2003/0118692, which is hereby incorporated by reference in its entirety. Examples of diacids include, but are not limited to, aromatic-diacids (e.g., terephthalic acid and carboxyphenoxypropane), C2-C20 alkyl-diacids, C2-C20 alkenyl-diacids, and mixtures thereof. The diacids may also include substituents as well. Reactive groups like amine and hydroxyl will increase the number of sites available for cross-linking Amino acids and other biomolecules will modify the biological properties of the polymer. Aromatic groups, aliphatic groups, and halogen atoms will modify the inter-chain interactions within the polymer.

In some embodiments, materials and composites comprise polymers of citric acid, polyethylene glycol, and glycerol 1,3-diglycerolate diacrylate. In some embodiments, citric acid, polyethylene glycol, and glycerol 1,3-diglycerolate diacrylate are polymerized to form a polymer (e.g., pre-polymer) of poly(polyethyleneglycol citrate) acrylate (PPCac). In some embodiments, materials and composites comprise polymers of citric acid, polyethylene glycol, glycerol 1,3-diglycerolate diacrylate, and N-isopropylacrylamide (NIPAAm). In some embodiments, PPCac and NIPAAm are reacted together to produce a poly(polyethyleneglycol citrate co N-isopropylacrylamide) (PPCN) polymer. In some embodiments, PPCN is provided as a material.

In some embodiments, polymers herein (e.g., PPCN or another polymer) comprise at least 0.1% citric acid monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% citric acid monomers (e.g., <99%, <98%, <95%, <90%, <80%, <70%, <60%, <50%, <40%, <30%, <20%, <10%, <5%, <4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% citric acid monomers.

In some embodiments, polymers herein (e.g., PPCN or another polymer) comprise at least 0.1% polyethylene glycol monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% polyethylene glycol monomers (e.g., <99%, <98%, <95%, <90%, <80%, <70%, <60%, <50%, <40%, <30%, <20%, <10%, <5%, <4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% polyethylene glycol monomers.

In some embodiments, polymers herein (e.g., PPCN or another polymer) comprise at least 0.1% glycerol 1,3-diglycerolate diacrylate monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% glycerol 1,3-diglycerolate diacrylate monomers (e.g., <99%, <98%, <95%, <90%, <80%, <70%, <60%, <50%, <40%, <30%, <20%, <10%, <5%, <4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% glycerol 1,3-diglycerolate diacrylate monomers.

In some embodiments, polymers and materials herein (e.g., PPCN or another polymer) comprise at least 0.1% N-isopropylacrylamide monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% N-isopropylacrylamide monomers (e.g., <99%, <98%, <95%, <90%, <80%, <70%, <60%, <50%, <40%, <30%, <20%, <10%, <5%, <4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% N-isopropylacrylamide monomers.

In some embodiments, provided herein are provided as composites of the polymers, hydrogels, materials described herein (e.g., poly(polyethyleneglycol citrate co N-isopropylacrylamide (PPCN)) with additional components. For example, materials may be used with one or more biodegradable polymers to form a composite material.

In some embodiments, a PPCN composite material comprises at least 0.1% PPCN (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, a PPCN composite material comprises less than 99% PPCN (e.g., <99%, <98%, <95%, <90%, <80%, <70%, <60%, <50%, <40%, <30%, <20%, <10%, <5%, <4%, <3%, <2%, <1%, <0.5%). In some embodiments, a PPCN composite material comprises PPCN in an amount of about 99%, about 98%, about 95%, about 90%, about 80%, about 70%, about 60%, about 50%, about 40%, about 30%, about 20%, about 10%, about 5%, about 4%, about 3%, about 2%, about 1%, about 0.5%, or ranges therein. The aforementioned percentages may be wt % or molar %.

Composites may also be made of PPCN (or other polymeric materials) and a non-biogregradable polymer, such as: silicone rubber, polyethylene, acrylic resins, polyurethane, polypropylene, and polymethylmethacrylate. Composites of PPCN and non-polymeric materials are also within the scope of embodiments described herein.

In some embodiments, synthesis of the polymers, hydrogels, networks, etc. described herein are produced by combination of the component molecules (e.g., citric acid, polyethylene glycol and glycerol 1,3-diglycerolate diacrylate; PPCac and NIPAAm, etc.) under the appropriate conditions (e.g., temperature, pressure, pH, etc.). In some embodiments, reaction, crosslinking, polymerization, etc. occurs upon combination of the components under appropriate conditions in the absence of any additional enzyme or chemical catalysts. In some embodiments, a radical initiator (e.g., AIBN) is used to induce a reaction or polymerization.

In some embodiments, components (e.g., citric acid, polyethylene glycol and glycerol 1,3-diglycerolate diacrylate; etc.) are heated to at least 100° C. (e.g., 100° C., 110° C., 120° C., 130° C., 140° C., 150° C., 160° C., 170° C., 180° C., 190° C., 200° C., or more). In some embodiments, components (e.g., PPCac and NIPAAm, etc.) are heated to at least 40° C. (e.g., 40° C., 50° C., 60° C., 70° C., 80° C., 90° C., 100° C., 110° C., 120° C., or more). In some embodiments, components are reacted at a temperature not exceeding 250° C. (e.g., <240° C., <220° C., <200° C., <180° C., <160° C., or less).

In some embodiments, components (e.g., citric acid, polyethylene glycol and glycerol 1,3-diglycerolate diacrylate; PPCac and NIPAAm, etc.) are reacted for at least 1 minute (e.g., >1 minute, >2 minutes, >3 minutes, >4 minutes, >5 minutes, >10 minutes, >20 minutes, >30 minutes, >45 minutes, >1 hour, >2 hours, >3 hours, >4 hours, >12 hours, >24 hours, >48 hours, >72 hours, or more).

In some embodiments, citric acid, polyethylene glycol and glycerol 1,3-diglycerolate diacrylate are reacted at a ratio of 5:9:1, 5:8:2, 5:7:3, 5:6, 4, 5:5:5, 4:9:2, 3:9:3, 2:9:4, 1:9:5, 6:8:1, 7:7:1, 8:6:1, 9:5:1, 10:4:1, 11:3:1, 12:2:1, 13:1:1, 4:10:1, 3:11:1, 2:12:1, 1:13:1, or any other suitable ratios thereof or rages there between. In some embodiments, PPCac and NIPAAm are reacted at a ratio of 10:1, 9:1, 8:1, 7:1, 6:1, 5:1, 4:1, 3:1, 2:1, 1:1, 1:2, 1:3, 1:4:1:5, 1:6, 1:7, 1:8, 1:9, 1:10, or any other suitable ratios thereof or rages there between.

In some embodiments, materials provided herein comprise a peptide component (e.g., conjugated to a polymer component) that is capable of one or more of: (i) binding to heparin/heparin sulfate, (ii) facilitating cell attachment to the material (e.g., via the integrin receptor), (iii) promoting cell migration into the material, (iv) enhancing cell proliferation, and/or (v) speeding wound closure when the material is administered to a wound. Experiments conducted during development of embodiments herein have demonstrated that the 12 amino acid peptide A5G81 (SEQ ID NO: 1; AGQWHRVSVRWG) performs particularly well (e.g., at the aforementioned criteria (i)-(v)) when incorporated into a material for treatment of wounds.

In some embodiments, A5G8-based peptides and/or peptide or polypeptide comprising an A5G81-based segment are provided herein. In some embodiments, such peptides and segments comprise a degree of sequence similarity and/or sequence identity with SEQ ID NO: 1 and/or exhibit one or more functional characteristics of A5G81, such as those demonstrated in the experiments conducted during development of embodiments herein.

In some embodiments, provided herein are peptides (e.g., conjugated to polymers and/or materials, as part of a polymer of material, etc.) for promoting cell migration and proliferation, and for promotion of wound healing. In some embodiments, peptides comprise at least 70% (e.g., 70%, 75%, 80%, 85%, 90%, 95%, 100%, and ranges therebetween) sequence similarity (e.g., allowing for conservative and/or semi-conservative substitutions) with SEQ ID NO: 1. In some embodiments, a peptide is provided comprising 0-12 (e.g., 0, 1, 2, 3, 4, 5, 6, 7, 8, 9, 10, 11, 12, or ranges therebetween) conservative and/or semi-conservative substitutions relative to SEQ ID NO: 1, and retaining or enhancing the wound healing characteristics of A5G81. In some embodiments, a peptide comprises fewer than five (e.g., 5, 4, <4, 3, <3, 2, <2, 1, or 0) non-conservative amino acid substitutions relative to SEQ ID NO: 1. In some embodiments, a peptide comprising SEQ ID NO: 1 is provided. In some embodiments, a peptide consisting of SEQ ID NO: 1 is provided.

In some embodiments, a peptide or polypeptide is provided comprising a portion comprising at least 70% (e.g., 70%, 75%, 80%, 85%, 90%, 95%, 100%, and ranges therebetween) sequence similarity (e.g., allowing for conservative and/or semi-conservative substitutions) with SEQ ID NO: 1. In some embodiments, a peptide segment is provided comprising 0-12 (e.g., 0, 1, 2, 3, 4, 5, 6, 7, 8, 9, 10, 11, 12, or ranges therebetween) conservative and/or semi-conservative substitutions relative to SEQ ID NO: 1, and retaining or enhancing the wound healing characteristics of A5G81. In some embodiments, a peptide or polypeptide is provided comprising a portion with fewer than five (e.g., 5, 4, <4, 3, <3, 2, <2, 1, or 0) non-conservative amino acid substitutions relative to SEQ ID NO: 1. In some embodiments, a or polypeptide is provided comprising SEQ ID NO: 1. In some embodiments, a peptide or polypeptide comprising a portion consisting of SEQ ID NO: 1 is provided.

In some embodiments, A5G81-based peptide and peptide-segments are provided, for example, for promotion of wound healing and/or tissue regeneration. In some embodiments, the A5G81-based peptide and peptide-segments described herein are further modified (e.g., substitution, deletion, or addition of standard amino acids; chemical modification; etc.). Modifications that are understood in the field include N-terminal modification, C-terminal modification (which protects the peptide from proteolytic degradation), alkylation of amide groups, hydrocarbon "stapling" (e.g., to stabilize conformations). In some embodiments, the peptides described herein may be modified by conservative residue substitutions, for example, of the charged residues (e.g., K to R, R to K, D to E and E to D) or the non-polar aliphatic (A to V, L, I, or M; V to A, L, I, or M; L to A, V, I, or M; I to M to A, V, L, or M; M to A, V, L, or I), etc. In some embodiments, such conservative substitutions provide subtle changes while preserving the local environment of the residue. Modifications of the terminal carboxy group include, without limitation, the amide, lower alkyl amide, constrained alkyls (e.g. branched, cyclic, fused, adamantyl) alkyl, dialkyl amide, and lower alkyl ester modifications. Lower alkyl is C1-C4 alkyl. Furthermore, one or more side groups, or terminal groups, may be protected by protective groups known to the ordinarily-skilled peptide chemist. The α-carbon of an amino acid may be mono- or dimethylated.

In some embodiments, one or more intra-peptide disulfide bonds are introduced (e.g., between two cysteines within a peptide/polypeptide). In some embodiments, the presence of an intra-peptide disulfide bond stabilizes the peptide.

Embodiments described herein may comprise A5G81-based peptidomimetics corresponding to the A5G81-based peptide and peptide-segments described herein with various modifications that are understood in the field. In some embodiments, residues in the peptide sequences described herein may be substituted with amino acids having similar characteristics (e.g., hydrophobic to hydrophobic, neutral to neutral, etc.) or having other desired characteristics (e.g., more acidic, more hydrophobic, less bulky, more bulky, etc.). In some embodiments, non-natural amino acids (or naturally-occurring amino acids other than the standard 20 amino acids) are substituted in order to achieve desired properties.

In some embodiments, residues having a side chain that is positively charged under physiological conditions, or residues where a positively-charged side chain is desired, are substituted with a residue including, but not limited to: lysine, homolysine, hydroxylysine, homoarginine, 2,4-diaminobutyric acid, 3-homoarginine, D-arginine, arginal (—COOH in arginine is replaced by —CHO), 2-amino-3-guanidinopropionic acid, nitroarginine (N(G)-nitroarginine), nitrosoarginine (N(G)-nitrosoarginine), methylarginine (N-methyl-arginine), ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexinic acid, p-aminobenzoic acid and 3-aminotyrosine and, histidine, 1-methylhistidine, and 3-methylhistidine.

A neutral residue is a residue having a side chain that is uncharged under physiological conditions. A polar residue preferably has at least one polar group in the side chain. In some embodiments, polar groups are selected from hydroxyl, sulfhydryl, amine, amide and ester groups or other groups which permit the formation of hydrogen bridges.

In some embodiments, residues having a side chain that is neutral/polar under physiological conditions, or residues where a neutral side chain is desired, are substituted with a residue including, but not limited to: asparagine, cysteine, glutamine, serine, threonine, tyrosine, citrulline, N-methylserine, homoserine, allo-threonine and 3,5-dinitro-tyrosine, and β-homoserine.

Residues having a non-polar, hydrophobic side chain are residues that are uncharged under physiological conditions, preferably with a hydropathy index above 0, particularly above 3. In some embodiments, non-polar, hydrophobic side chains are selected from alkyl, alkylene, alkoxy, alkenoxy, alkylsulfanyl and alkenylsulfanyl residues having from 1 to 10, preferably from 2 to 6, carbon atoms, or aryl residues having from 5 to 12 carbon atoms. In some embodiments, residues having a non-polar, hydrophobic side chain are, or residues where a non-polar, hydrophobic side chain is desired, are substituted with a residue including, but not limited to: leucine, isoleucine, valine, methionine, alanine, phenylalanine, N-methylleucine, tert-butylglycine, octylglycine, cyclohexylalanine, β-alanine, 1-aminocyclohexylcarboxylic acid, N-methylisoleucine, norleucine, norvaline, and N-methylvaline.

In some embodiments, peptide and polypeptides are isolated and/or purified (or substantially isolated and/or substantially purified). Accordingly, in such embodiments, peptides and/or polypeptides are provided in substantially isolated form. In some embodiments, peptides and/or polypeptides are isolated from other peptides and/or polypeptides as a result of solid phase peptide synthesis, for example. Alternatively, peptides and/or polypeptides can be substantially isolated from other proteins after cell lysis from recombinant production. Standard methods of protein purification (e.g., HPLC) can be employed to substantially purify peptides and/or polypeptides. In some embodiments, the present invention provides a preparation of peptides and/or polypeptides in a number of formulations, depending on the desired use. For example, where the peptide is substantially isolated (or even nearly completely isolated from other proteins), it can be formulated in a suitable medium solution for storage (e.g., under refrigerated conditions or under frozen conditions). Such preparations may contain protective agents, such as buffers, preservatives, cryprotectants (e.g., sugars such as trehalose), etc. The form of such preparations can be solutions, gels, etc. In some embodiments, peptides and/or polypeptides are prepared in lyophilized form. Moreover, such preparations can include other desired agents, such as small molecules or other peptides, polypeptides or proteins. Indeed, such a preparation comprising a mixture of different embodiments of the peptides and/or polypeptides described here may be provided.

In some embodiments, provided herein are peptidomimetic versions of the peptide sequences described herein or variants thereof. In some embodiments, a peptidomimetic is characterized by an entity that retains the polarity (or non-polarity, hydrophobicity, etc.), three-dimensional size, and functionality (bioactivity) of its peptide equivalent but wherein all or a portion of the peptide bonds have been replaced (e.g., by more stable linkages). In some embodiments, 'stable' refers to being more resistant to chemical degradation or enzymatic degradation by hydrolytic enzymes. In some embodiments, the bond which replaces the amide bond (e.g., amide bond surrogate) conserves some properties of the amide bond (e.g., conformation, steric bulk, electrostatic character, capacity for hydrogen bonding, etc.). Chapter 14 of "Drug Design and Development", Krogsgaard, Larsen, Liljefors and Madsen (Eds) 1996, Horwood Acad. Publishers provides a general discussion of techniques for the design and synthesis of peptidomimetics and is herein incorporated by reference in its entirety. Suitable amide bond surrogates include, but are not limited to: N-alkylation (Schmidt, R. et al., Int. J. Peptide Protein Res., 1995, 46,47; herein incorporated by reference in its entirety), retro-inverse amide (Chorev, M. and Goodman, M., Acc. Chem. Res, 1993, 26, 266; herein incorporated by reference in its entirety), thioamide (Sherman D. B. and Spatola, A. F. J. Am. Chem. Soc., 1990, 112, 433; herein incorporated by reference in its entirety), thioester, phosphonate, ketomethylene (Hoffman, R. V. and Kim, H. O. J. Org. Chem., 1995, 60, 5107; herein incorporated by reference in its entirety), hydroxymethylene, fluorovinyl (Allmendinger, T. et al., Tetrahydron Lett., 1990, 31, 7297; herein incorporated by reference in its entirety), vinyl, methyleneamino (Sasaki, Y and Abe, J. Chem. Pharm. Bull. 1997 45, 13; herein incorporated by reference in its entirety), methylenethio (Spatola, A. F., Methods Neurosci, 1993, 13, 19; herein incorporated by reference in its entirety), alkane (Lavielle, S. et. al., Int. J. Peptide Protein Res., 1993, 42, 270; herein incorporated by reference in its entirety) and sulfonamido (Luisi, G. et al. Tetrahedron Lett. 1993, 34, 2391; herein incorporated by reference in its entirety).

Suitable peptidomimetics may involve the replacement of larger structural moieties with di- or tripeptidomimetic structures and in this case, mimetic moieties involving the peptide bond, such as azole-derived mimetics may be used as dipeptide replacements. Suitable peptidomimetics include reduced peptides where the amide bond has been reduced to a methylene amine by treatment with a reducing agent (e.g. borane or a hydride reagent such as lithium aluminumhydride); such a reduction has the added advantage of increasing the overall cationicity of the molecule.

Other peptidomimetics include peptoids formed, for example, by the stepwise synthesis of amide-functionalized polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142; herein incorporated by reference in its entirety.

In some embodiments, the A5G81-based peptide and peptide-segments that are disclosed herein may be further derivatized by chemical alterations, such as amidation, deamidation, glycosylation, acylation, sulfation, phosphorylation, acetylation, and cyclization. Such chemical alterations can be imparted through chemical or biochemical methodologies, as well as through in vivo processes, or any combination thereof.

In certain embodiments, the A5G81-based peptide and peptide-segments described herein are derivatized by modification of the terminal amino group. Such modifications include, without limitation, the desamino, N-lower alkyl, N-di-lower alkyl, constrained alkyls (e.g. branched, cyclic, fused, adamantyl) and N-acyl modifications where the acyl moiety is C6-C20 alkyl.

In certain embodiments, the A5G81-based peptide and peptide-segments described herein are derivatized by modification of the terminal carboxyl group. Such modifications include, without limitation, amide, lower alkyl amide, constrained alkyls (e.g. branched, cyclic, fused, adamantyl) alkyl, dialkyl amide, and lower alkyl ester modifications, where lower alkyl is C1-C4 alkyl. Furthermore, one or more side groups, or terminal groups, may be protected by protective groups known to the ordinarily-skilled peptide chemist. The α-carbon of an amino acid may be mono- or dimethylated.

In some embodiments, the peptides described herein are covalently conjugated to polymer or other material, e.g., for use in a composition or device for the promotion of wound healing. In experiments conducted during development of embodiments herein, peptides were synthesized with a terminal cysteine residue (e.g., not present in natural laminin sequences) for conjugation to a polymer (e.g., PPCN) via the hetero-bifunctional cross linker N-[β-maleimidopropionic acid] hydrazide (BMPH). In some embodiments, cysteine-terminated peptides may be conjugated to polymers (e.g., displaying appropriate functional groups) directly or via other linkers. In some embodiments, unmodified (e.g., without terminal cysteines) peptides are conjugated to polymers (e.g., directly or via a linker) using an amino acid reside already present in the peptide sequence. In some embodiments, peptides are modified (e.g., chemically, by amino acid substitution (e.g., with a natural (e.g., cysteine, lysine, etc.) or unnatural amino acid), by addition of a terminal amino acid (e.g., a natural (e.g., cysteine, lysine, etc.) or unnatural amino acid), etc.) for conjugation (e.g., directly or via a chemical linker) to a polymer.

Conjugation via a terminal cysteine and BMPH provided as suitable conjugation chemistry for use in the examples herein. However, embodiments within the scope herein are not so limited.

In some embodiments, peptides and polymers are conjugated by click chemisty, employing Diels-Alder reactions, thiol-yne reactions, and azide-alkyne reactions, thiol/maleimide, thiol/haloacetyl (e.g., iodoacetyl, etc.), azide/phosphine (Staudinger ligation), thiol/pyridyl disulfide (e.g. pyridyldithiol, etc.), sulphonyl azides/thio acids, etc. In some embodiments, a conjugation of the peptide and polymer comprises a reaction pair selected from: maleimide/thiol, succimidylester (NHS ester)/amine, azide, carboxy/EDC (1-Ethyl-3-[3-dimethylaminopropyl]carbodiimide Hydrochloride)/amine, amine/Sulfo-SMCC (Sulfosuccinimidyl 4-[N-maleimidomethyl]cyclohexane-1-carboxylate)/thiol, and amine/BMPH(N-[β-Maleimidopropionic acid]hydrazide)/thiol. Other conjugation pairs, reaction chemistries, etc. are within the scope herein The materials described herein find use in a variety of fields, and may be used in any suitable applications use. In some embodiments, materials (e.g. displaying laminin peptides (e.g., A5G81 or A5G81-based peptides)) find use in any suitable wound healing and/or tissue regeneration application.

In some embodiments, materials are configured for application directly to a wound or other in vivo site (e.g., damaged tissue, diseased site, surgical site, etc.). In some embodiments, the thermoresponsive and/or adhesive properties materials herein allow for the material to stay in place upon application to the wound. In some embodiments, thermoresponsive properties of the materials allow for application to the wound as a liquid (e.g., at room temperature) followed by gelling of the material upon temperature increase to physiologic conditions. In some embodiments, a composition comprising such materials is shaped to fit on or within a wound. Compositions may be applied in the form of an amorphous gel, a wafer, a thin sheet, etc. In some embodiments, an adhesive is applied to the composition (e.g., the boarders of the material) to assist in securing materials herein to the wound.

In some embodiments, the materials herein (e.g. displaying laminin-based peptides) comprises or is applied to the wound-contacting face of a wound dressing. Suitable wound dressings include gauze, a bandage, a film dressing, a pad, membrane, etc. Suitable dressings that may be used in conjunction with embodiments herein (e.g., modified to have a wound-contacting face comprising materials described herein) include, for example, those described in: U.S. Pat. No. 4,732,146 to Fasline et al., U.S. Pat. No. 4,917,112 to Kalt, U.S. Pat. No. 4,909,243 to Frank et al., U.S. Pat. No. 4,907,579 to Kum, U.S. Pat. No. 5,167,613 to Karami et al., U.S. Pat. No. 3,779,242 to McCullough, U.S. Pat. No. 4,709,695 to Kohn et al., U.S. Pat. No. 4,399,816 to Spangler, U.S. Pat. No. 5,086,763 to Hathman, and U.S. Pat. No. 4,926,883 to Strock, all of which is herein incorporated by reference in their entireties.

In some embodiments, the materials herein are configured to deliver additional agents (e.g., therapeutic agents, etc.). In some embodiments, agents are embedded within a material during formation of the composite. In other embodiments, an agent is embedded within a material post-preparation (e.g., by soaking). In some embodiments, a laminin-based peptide displaying polymeric material is coated in an agent. In some embodiments, an additional agent is one that provides additional functionality to the composite (e.g., wound healing, tissue repair, antibacterial, antiseptic. analgesic, etc.).

In some embodiments, additional agents may be coated onto a device, composition or material herein. In some embodiments, additional agent may be conjugated to materials herein. In some embodiments, additional agents may be soaked and/or embedded within materials herein.

Additional agents may augment one or more aspects of wound healing that are not addressed by the materials described herein. Alternatively, additional agents may enhance a characteristic of the materials described herein. In some embodiments, material herein are provided with additional agents coated onto the materials, embedded within the materials, conjugated to the materials, etc. In some embodiments, materials described herein are not modified by the inclusion of additional agents, but are used in wound healing methods with such additional agents. In some embodiments, exemplary agents useful for treating wounds in embodiments herein include agents such as: immunostimulating agents (e.g., Betafectin™), antiviral agents, antikeratolytic agents, anti-inflammatory agents, antifungal agents, tretinoin, sunscreen agents, dermatological agents, topical antihistamine agents, antibacterial agents, bioadhesive agents, respiratory bursting inhibitors (lactic acid, adenosine), inhibitors of prostaglandin synthesis (e.g., ibuprofen, aspirin, indomethacin, meclofenomic acid, retinoic acid, padimate O, meclomen, oxybenzone), steroidal anti-inflammatory agents (e.g., corticosteroids including synthetic analogs), antimicrobial agents (e.g., neosporin ointment, silvadine), antiseptic agents, anesthetic agents (e.g., pramoxine hydrochloride, lidocaine, benzocaine), cell nutrient media, burn relief medications, sun burn medications, acne preparations, insect bite and sting medication, wound cleansers, wound dressings, scar reducing agents (e.g., vitamin E), and the like, and mixtures thereof.

In some embodiments, materials herein are configured for delivery to a subject. In some embodiments, they are administered at the surface of a wound. In other embodiments, they are applied subdermally or otherwise injected beneath a wound.

Embodiments described herein find use, for example, as dressing for wound healing and repair in diabetics or healthy individuals, and/or as a delivery vehicle for cell-based therapies.

Embodiments described herein have advantages of, for example, intrinsic antioxidant properties, a laminin-derived peptide that is conjugated to the material in a specific orientation is significantly increases wound closure rate, and/or versatile chemistry can be used with a wide variety of peptides to provide functionality to the polymer.

The PPCN-peptide hydrogel disclosed herein overcomes obstacles in the field by supporting efficient cell migration into the wound while minimizing oxidative stress.

Experiments were conducted during development of embodiments of the present invention to evaluate the in vitro and in vivo performance of a novel wound dressing composed of a thermoresponsive hydrogel with intrinsic antioxidant activity conjugated with the laminin-derived adhesion peptide A5G81. This peptide hydrogel can be used to provide a most environment with intrinsic free radical scavenging properties, incorporating cell-targeting peptides to stimulate cell infiltration and wound closure without the need for soluble factors.

EXPERIMENTAL

Example 1

Materials and Methods

Peptide Synthesis and Characterization

Cysteine-terminated peptides were synthesized manually on Fmoc-Rink amide MHBA resin using a standard solid phase peptide synthesis protocol. They were purified using reverse-phase HPLC with a C18 column, and the final products were characterized by matrix-assisted laser desorption/ionization time of flight mass spectrometry (MALDI-TOF MS). Self-assembled monolayer cell adhesion assay was performed (ref 56; incorporated by reference in its entirety). Maleimide-terminated alkanethiol was self-assembled on the gold surfaces to form the well-organized monolayer. Known amount of characterized Cysteine-terminated peptides were dissolve in 0.1% trifluoroacetic acid solution and incubate with the surface to allow peptide absorption on the surface via thiol-maleimide reaction. The resulting surfaces were characterized by MALDI-TOF MS for peptide adsorption before being used for HDFs and HEKas adhesion studies. The adherent cells were counted 2 hours after the initial seeding.

PPCN Synthesis and Peptide Conjugation

PPCN was synthesized (ref 29; incorporated by reference in its entirety). First, poly(polyethyleneglycol citrate) acrylate prepolymer (PPCac) was synthesized by a polycondensation reaction at 140° C. for 45 min under constant stirring at 300 rpm. The resulting solution was cooled to room temperature. Then, N-isoproylacrylamide monomer (NIPAM) was added to the PPCac prepolymer at a 1:1 w/w ratio and dissolved in 1,4-dioxane. The free radical initiator 2,2-azobisisobutyronitrile (AIBN) was added to the system after both PPCac and NIPAM were fully dissolved. Free radical polymerization was allowed to progress for 8 hours at 65° C. under nitrogen. The resulting PPCN copolymer was dissolved in 1,4-dioxane, purified by precipitation in diethyl ether and vacuum-dried.

Peptide conjugation to PPCN was performed using the hetero-bifunctional cross linker N-[β-maleimidopropionic acid] hydrazide (BMPH). The carboxyl group on PPCN was activated by 3 equivalents of 1-ethyl-3-[3-dimethylaminopropyl] carbodiimide hydrochloride (EDC) and 15 equivalents of N-hydroxysuccinimide (NHS) for 10 minutes before adding the BMPH linker. The mixture was allowed to react for 1.5 hours. The resulting linker-conjugated PPCN was dialyzed, flash-frozen and lyophilized. BMPH-conjugated PPCN was tested by $1^H$-NMR, as well as FTIR. The extent of functionalization was measured by reacting BMPH-PPCN with cysteine. This reaction was monitored with Ellman's reagent to measure the consumption of free thiols via changes in absorbance at 405 nm.

BMPH-PPCN was then dissolved in 2-(N-morpholino)ethanesulfonic acid (MES) buffer solution (pH 6.0) and mixed with PPCN to obtain a 1:10 BMPH to PPCN molar ratio. Peptide was then added to the BMPH-PPCN solution at a 1:10 peptide to PPCN molar ratio and reacted for 2 hours. The extent of peptide conjugation was again evaluated by monitoring the consumption of free thiols using Ellman's reagent. The final product was flash frozen and lyophilized. Peptide-conjugated PPCN was characterized by matrix-assisted laser desorption/ionization mass spectrometry (MALDI).

Determination of the Lower Critical Solution Temperature

The lower critical solution temperatures of the PPCN and PPCN-peptide hydrogels were determined using a Discovery Hybrid Rheometer (TA Instruments, DE). The storage and loss moduli of the gels were measured at a frequency of 1 Hz and a heating rate of 1° C./min, using a 2% amplitude and a 6 $s^{-1}$ angular frequency in the range from 15° C. to 40° C. The LCST was obtained from the crossing point of the loss and storage modulus curves.

Antioxidant Activity Assessment

The antioxidant activity of the PPCN-peptide hydrogels was determined using the β-carotene-linoleic acid assay (ref 29; incorporated by reference in its entirety).

In Vitro 3D Cell Culture

Human epithelial keratinocytes (HEKa) or human dermal fibroblasts (HDF) were mixed with cold PPCN-peptide solutions (100K cells/mL gel), added to wells of uncoated slides (ibidi, WI) and allowed to gel at 37° C. for 1-2 min. Cell culture medium (KGM-Gold for HEKa, DMEM+10% FBS for HDF) was then added to each well, and cells were cultured at 37° C. and 5% $CO_2$. After 5 or 10 days, the gels were washed twice with warm 1×PBS, and stained with live/dead stain (2 uM calcein AM and 2 uM ethidium homodimer-1) at 37° C. for 15 min. The samples were then washed twice with warm 1×PBS and imaged on a Nikon C2 Confocal microscope.

SAM Preparation

Glass coverslips were first coated with 2 nm Ti, followed by 11 nm Au using an electron beam evaporator. The gold-coated surfaces were soaked overnight at 4° C. in a 1 mM mixture of 1% maleimide-terminated and 99% tri (ethylene glycol)-terminated disulfides. The SAM coverslips were rinsed with ethanol, water, then ethanol, dried under a nitrogen stream and cut into approximately 1×1 cm chips for use in cell culture experiments.

Cell Adhesion Assay

The synthesized peptides were immobilized onto SAM chips by incubating the chips with 100 μM peptide solution in PBS at room temperature for 1 hr. The peptide chips were then rinsed three times with PBS, and cells were immediately seeded on the surfaces at a density of 20,000 cells/$cm^2$. Cells were incubated at 37° C. and 5% $CO_2$ for 1 hr to allow attachment. The surfaces were then rinsed with PBS and the adherent cells were fixed in 4% paraformaldehyde. Peptide chips were then mounted with Vectashield+DAPI and imaged on a Nikon Eclipse TE2000-U inverted fluorescence microscope. The number of cells per field of view was counted using ImageJ software. The cell number per area for each chip was based on the average of 5 fields of view.

PicoGreen Total DNA Quantification Assay

HDF encapsulated hydrogel scaffold samples were prepared and cultured using the same method as the in vitro 3D cell culture with 10 K cells per 50 μl hydrogel per sample. At each time point, after removing the medium, the samples were cooled on ice, and the cells were lysed by PBS-3% Triton-X. The Quant-iT PicoGreen dsDNA assay kit (Life Technologies) was employed according to the manufacturer's protocol, and the results were read in triplicates. Samples of 100 mL were accessed using microplate reader (Tecan, Männedorf, Switzerland); fluorescence was quantified at 520 nm with excitation at 480 nm.

Cell Cycle Analysis

A flow cytometric analysis, with propidium iodide (PI), was performed in order to measure the cell cycle activity. At each time point, cell encapsulated scaffolds were liquefied, and the cells were extracted via centrifuging. The cells were then washed with ice-cold PBS, and fixed with 70% ice-cold ethanol for 1 h before repeated washing with PBS and re-suspension in PBS with 0.5 mg/mL Rnase A (Thermo Fisher Scientific). After 1 h incubation, the cellular DNA was then stained with PI (50 μg/mL) for 20 min while protected from the light at 4° C. The relative DNA concentration of the stained cells was measured using a BD LSRII flow cytometer (Becton Dickinson, San Jose, Calif.).

Proliferation Inhibition

The mouse monoclonal antibody against human integrin α6 and α3 were purchased from Santa Cruz (Dallas, T A), and dialyzed with 10,000 MWCO Dialysis Cassettes dialysis cassette (Thermo Scientific) overnight to remove the sodium azide. For the proliferation inhibition study, P-A5G81 and PPCN hydrogel scaffolds were prepared as 100 mg/ml PBS solution as described above. Before cell encapsulation, HDFs were pre-incubated in suspension with corresponding anti-integrin antibodies (final concentration 10 μg/mL) for 15 min at 37° C. Then the pre-treated HDFs ($1\times10^4$ cells per 50 μL scaffold per well) were incubated on the ultra-low attachment plate (Coring, Coring, NY) for 5 days at 37° C. in 5% $CO_2$. Anti-integrin antibodies treatments were also added in the culture media for the corresponding groups (10 μg/mL), and the media was changed every other day. After 5 days of incubation, total DNA content within each scaffold was quantified using PicoGreen DNA quantification assay as mentioned above.

Diabetic Wound Healing Model

The in vivo performance of the PPCN-peptide gels was evaluated with a splinted excisional wound model (ref 46; incorporated by reference in its entirety) in db/db mice (BKS.Cg-Dock7$^m$+/+Lepr$^{db}$/J Homozygous for Lepr$^{db}$).

The animals were separated into 3 groups of five, with each group receiving one of the following treatments: (1) P-A5G81 vs. P-RGD, (2) P-A5G81 vs. P-IP (inactive peptide), or (3) P-A5G81 vs. PPCN. To prevent skin contraction, paired pre-sterilized doughnut-shaped splints (10-mm inner diameter; 12-mm outer diameter) made from 0.5-mm-thick acrylate tape (3M, St. Paul, Minn.) were attached to the left and right dorsal sides of the mouse with Vetbond (3M) and interrupted 6-0 nylon sutures (Ethicon, Cincinnati, Ohio) after depilation. A 6-mm circular, full-thickness wound was made in the center of each splinted area. 40 µl of gel solution was applied to each wound bed. A transparent sterile occlusive dressing TegaDerm™ (3M) was then placed over the wound and the splint. Digital images of the wound area were taken every other day, and quantified in ImageJ by normalizing the wound area to the known splint area at each time point. Hydrogel dressings were reapplied on day 6, after gently rinsing the wound with cold 1× PBS.

Tissue Processing and Histology

Upon full closure of the wounds (for the first batch study) or 10 days after the initial wound surgery (for the second batch study), animals were euthanized and the regenerated wound tissue was excised with a 10-mm biopsy punch (Acuderm, Fort Lauderdale, Fla.), fixed using 4% paraformaldehyde and embedded by paraffin. The tissues were then sectioned and processed for hematoxylin and eosin (H&E) staining to measure granulation tissue thickness, and the epithelial gap histomorphometrically. The granulation tissue thickness and epithelial gap was measured based on 5 different H&E images for each group by blinded observer using ImageJ. The tissue sections were also stained for Keratin 10, Integrin α3 or F4/80 (Santa Cruz, Dallas, Tex.) The secondary antibodies used were either conjugated to AlexaFluor488 or AlexaFluor555 (Invitrogen, Carlsbad, Calif.).

Statistical Analyses

Statistical analyses were performed using GraphPad Prism 6.0c. Two-way ANOVA tests were used to measure differences for experiments with multiple data sets with a Tukey test performed between groups with significant differences to correct for the multiple pair-wise comparisons. A value of $p \leq 0.05$ was considered to be statistically significant.

Example 2

Results

Full Amino-Acid Sequence is Required for A5G81 Bioactivity

The peptide A5G81 is a 12-amino-acid sequence derived from the α5 globular domain of laminin (ref 30-32; incorporated by reference in their entireties). It exhibits excellent cell adhesive properties (refs. 30-33; incorporated by reference in their entireties) and facilitates adhesion through integrins α3β1 and α6β1 (31, 33). This adhesion profile is quite different than the commonly used fibronectin-derived RGD adhesion sequence, which is known to interact with all 5 αV-containing integrins, as well as α5β1, α8β1 and αIIbβ3 (ref 34; incorporated by reference in its entirety). There is evidence that laminin-derived peptides can enhance wound healing (refs. 5, 35; incorporated by reference in their entireties), and the activation of α3β1 integrin is essential for dermal fibroblasts migration and epidermis keratinocytes re-epithelialization on the wound (refs. 36-41; incorporated by reference in their entireties). Despite the extensive use of RGD in the field, and its interaction with significantly more integrins, experiments were conducted during development of embodiments herein to determine whether A5G81 would promote cell migration, proliferation, and spreading within a wound in order to increase wound closure rates. A self-assembled monolayer (SAM) adhesion assay was utilized to find the minimal binding sequence of this peptide. The cell types used (human dermal fibroblasts and human epithelial keratinocytes) were chosen based on their relevancy to wound healing. The full A5G81 sequence had excellent cell adhesion properties. Amino-acid truncations resulted in a drastic loss of adhesion (FIG. 1a), indicating that the full peptide sequence is desired to maintain the full bioactivity of A5G81. The loss of adhesion was also significant after Ala substitution of individual residues (FIG. 1b), further supporting the conclusion that the unique combination of the 12 amino acid sequence provides optimized maintenance of cell adhesion. The full A5G81 peptide was therefore conjugated to the PPCN material and used for additional experiments. A hydrogel containing an inactive form of A5G81 (WHRVSVC (SEQ ID NO: 13), IP) with very low cell adhesive properties served as a negative control. A PPCN-RGD gel was used as a positive control for cell adhesion within the gel.

Peptide Conjugation to PPCN Hydrogel Via "Click" Chemistry

Figure 2:
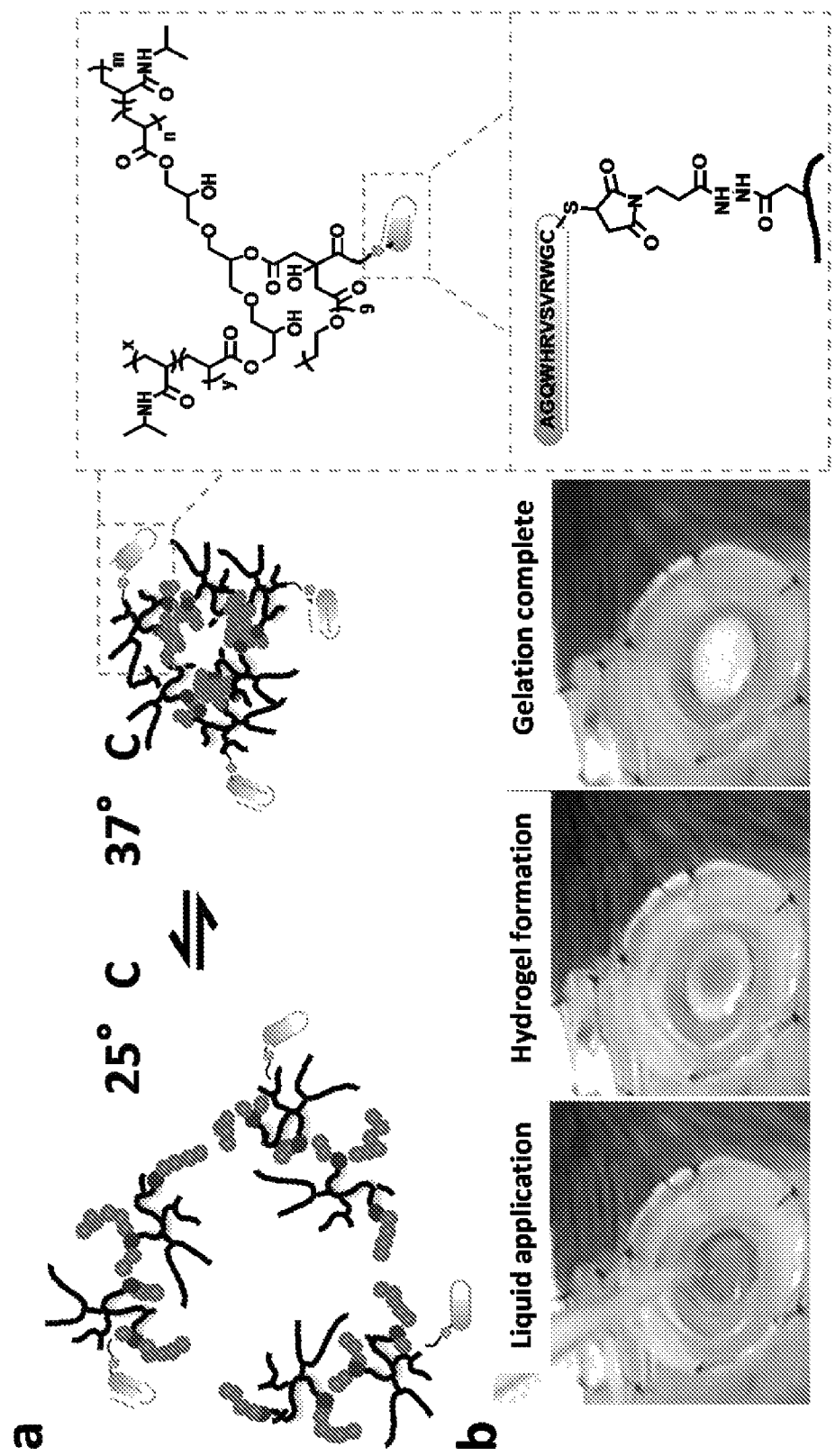
FIG. 2. The thermoresponsive and antioxidant properties of PPCN are preserved after peptide immobilization. (a) Schematic illustrating the thermoresponse of the P-A5G81 when transition from room temperature to 37° C. (Left), and the A5G81 peptide modification (SEQ ID NO: 2) via the maleimide-and-hydrazide crosslinker BMPH (right). (b) P-A5G81 hydrogel is highly moldable, and can be applied in liquid form to achieve the full coverage of the wound bed. (c) Rheological measurements showed that peptide immobilization slightly lowers the LCST of PPCN. (d) β-carotene lipid peroxidation assay showed improved antioxidant activity of the peptide-modified PPCN. Statistical significance performed using one-way ANOVA with a Dunnet multiple comparison test (*p<0.05; p<0.01; *p<0.001).
Figure 2:
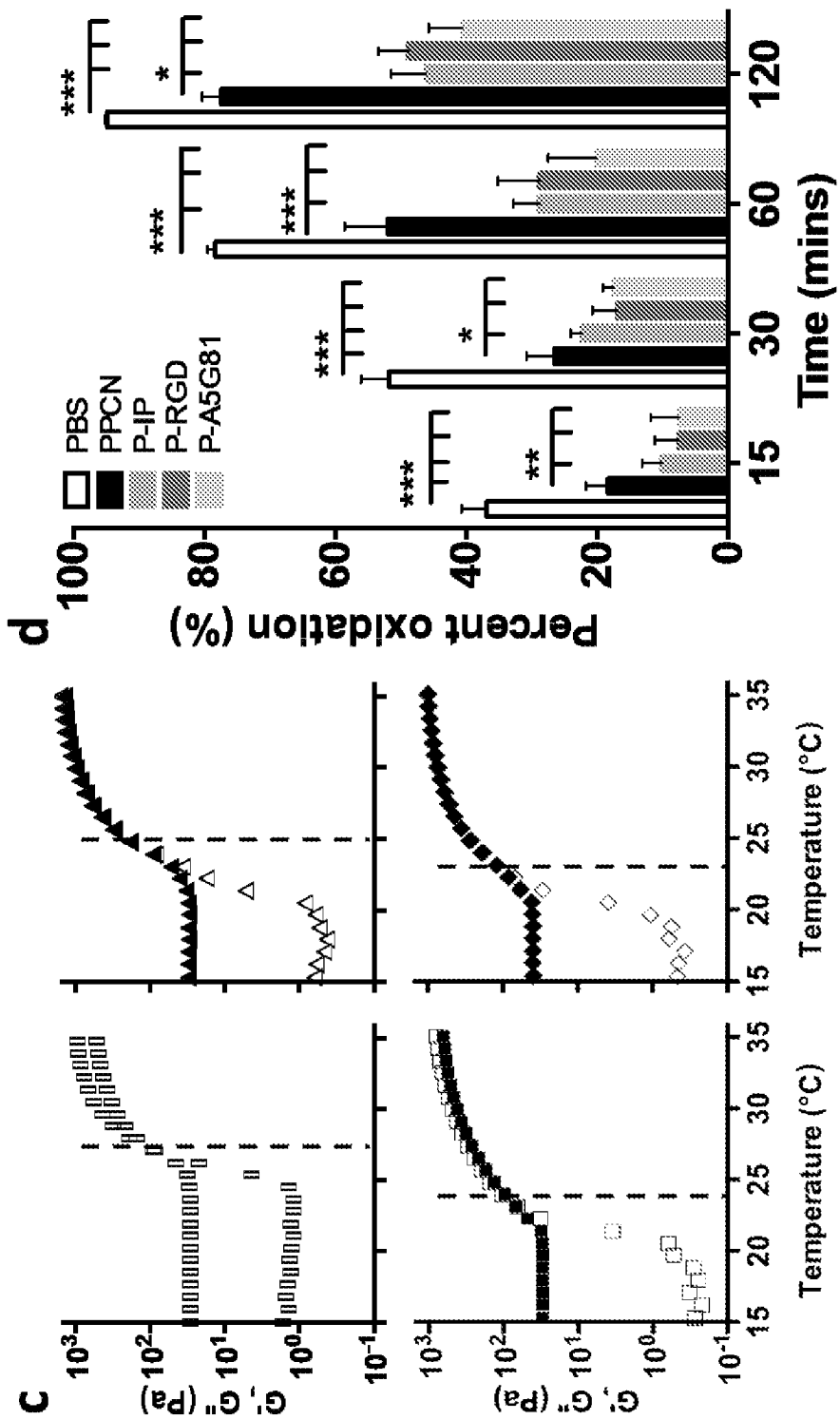

The thermoresponsive PPCN hydrogel was synthesized as described previously described (29). Peptides were conjugated to the PPCN polymer based on the schematic in FIG. 2a. Conjugation was achieved using a bifunctional linker (BMPH) that reacted with the carboxyl groups on PPCN and the thiol group present in peptides with terminal Cysteine residues. It is important to note that with this method, the peptide is always conjugated at its terminal residue, thus preserving its desired orientation and bioactivity. The successful conjugation was confirmed using matrix-assisted laser desorption/ionization mass spectrometry (MALDI) (supporting material). Signature peaks of peptide+BMPH and peptide+BMPH+citric acid were easily identifiable, indicating the successful conjugation of peptides to PPCN. After the modification, the resulting hydrogel still kept its thermoresponsiveness. Due to the thermoresponsive properties, such hydrogel can be kept and applied on to the wound bed as a solution, and the gelation happens within seconds upon exposure to body temperature (FIG. 2b). Such process is reversible by rinsing the hydrogel covered wound with cold saline solution. Due to such property, reapplication can be easily performed without disturbing the regenerated tissue.

Thermoresponsive and Antioxidant Properties of PPCN-Peptide Dressings

The lower critical solution temperature (LCST) of the PPCN-peptide materials was determined from rheological measurements as the temperature at which the loss and storage modulus curves first intersect (FIG. 2c). Peptide conjugation slightly lowered the LCST (23-24 vs. 27° C.) of the PPCN material. These phase transition temperatures are within the acceptable range to ensure that the material can be applied as a cooled liquid, which would form a hydrogel scaffold upon contact with tissue at the wound bed.

A lipid peroxidation inhibition assay was used to determine how peptide conjugation affects the antioxidant properties of the PPCN material. The results show that addition of peptides inhibited lipid peroxidation to a greater extent when compared with the PPCN material alone (FIG. 2d). There is a significant evidence that antioxidant hydrogel materials can improve wound healing (refs. 4, 42-45; incorporated by reference in their entireties). The thermoresponsive properties, in combination with the covalent incorporated ECM-derived peptides are expected to provide an optional microenvironment to facilitate cell proliferation that promotes regeneration of the granulation tissue, make material herein particularly suitable for wound healing applications.

Figure 3:
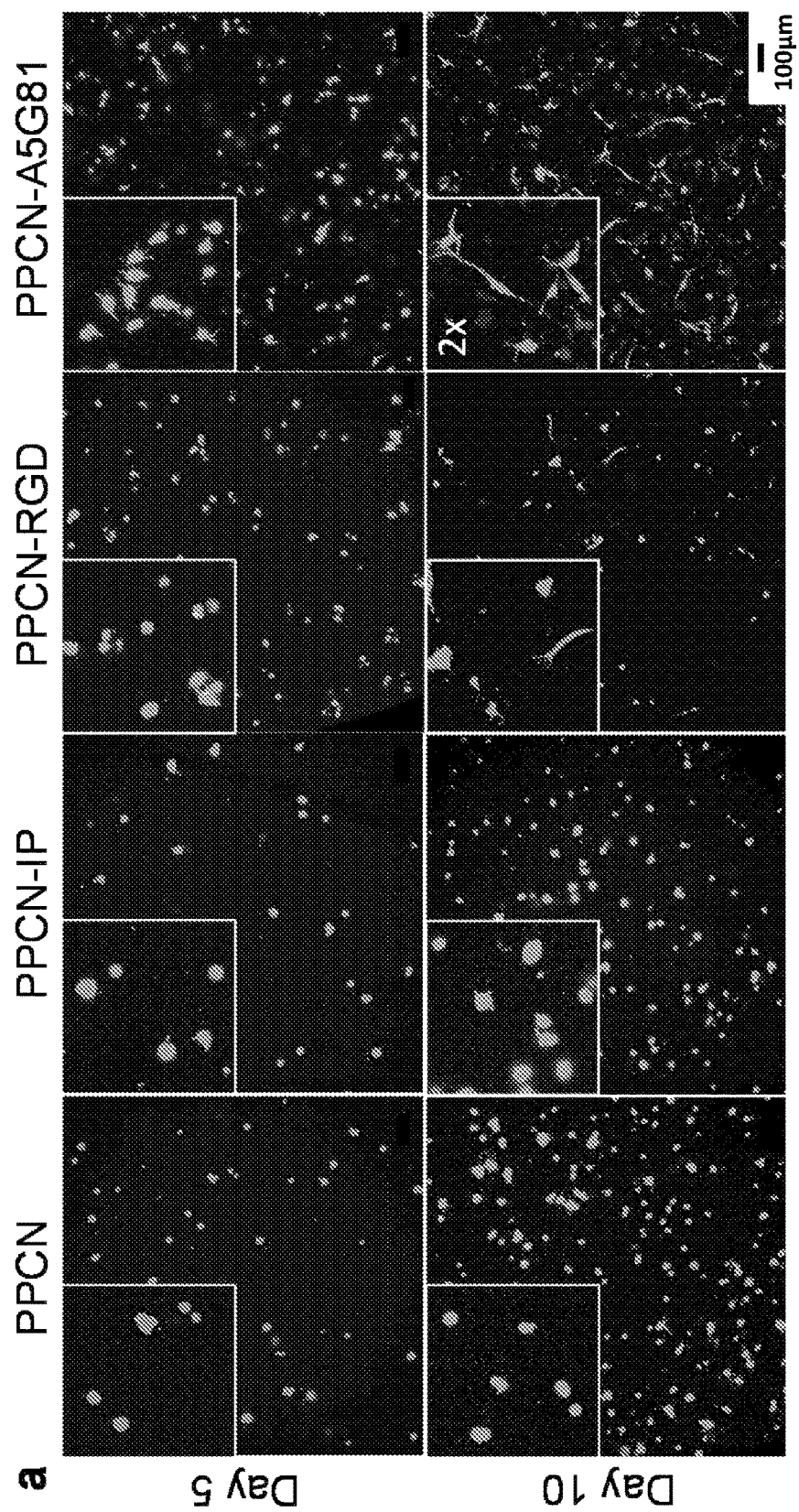
FIG. 3. P-A5G81 promotes the spreading and proliferation of the HDFs seeded inside. (a) HDFs seeded inside the gels were stained with live/dead assay and imaged using a confocal microscope. Maximum projection images of all groups at 5 and 10 days (scale bar: 100 µm). Inserts show a 2× magnified view of cell spreading. (b) Cells proliferate within the hydrogel scaffold. (c) Cell cycle analysis of the HDFs seeded inside the gels. Statistical significance performed using one-way ANOVA with a Dunnet multiple comparison test (n≥5; *p<0.05; p<0.01; *p<0.001).
Figure 3:
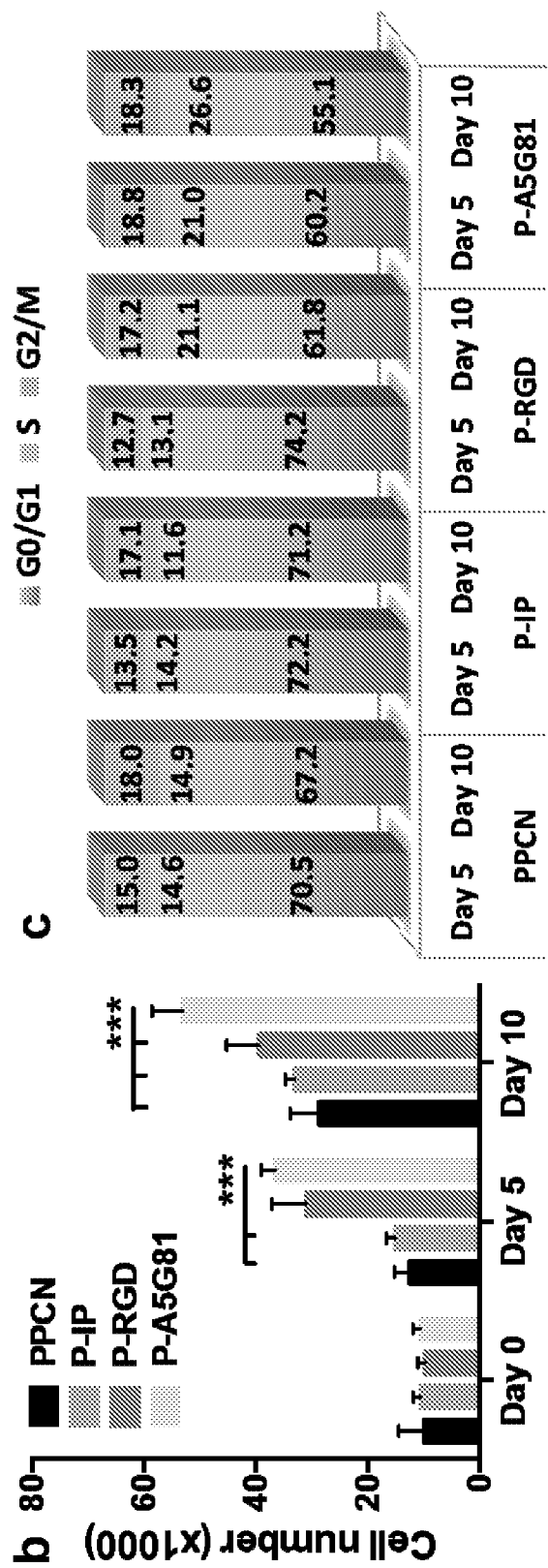

PPCN-A5G81 Gels Promotes Cell Spreading and Proliferation in an In Vitro 3D Culture The incorporation of A5G81 peptide into the PPCN hydrogel facilitated cell spreading in 3D in vitro culture (FIG. 3a). Human dermal fibroblasts seeded in PPCN-A5G81 gels began to spread at day 5, and were fully elongated with typical fibroblast morphology at day 10. Similar results were observed with the PPCN-RGD gels. This is a drastic improvement when compared to cells in the polymer gel without peptides, which did not spread significantly at day 10. The incorporation of an inactive segment of A5G81 did not support cell spreading, and the cell morphology remained similar to that observed in the PPCN gel. These findings confirm that adhesion is facilitated through specific ligand-receptor interactions with the full A5G81 peptide.

Upon identifying the HDFs' morphology within the PPCN-peptide scaffold, the cellular activity of these cells were analyzed by cell cycle analysis and their proliferation of was monitored by quantifying the total DNA content within the gel overtime (FIG. 3b). At both day 5 and 10, cell cycle profile indicates a significant higher portion of DNA synthesis phase (S phase) cells in P-A5G81 gel (FIG. 3c) comparing to the others. This S phase percentage increased from 21% to 26.6% from day 5 to day 10 in the P-A5G81 group. Similar pattern was also observed in the P-linRGD group, while the percentage of cells in S phase stayed relative constant in PPCN and P-inactive scaffolds. P-A5G81 gel also supports a higher cell proliferation rate over the course of 10 days (FIG. 3b), which further supports P-A5G81 gel promotion of HDFs proliferation in in vitro 3D culture.

Figure 4:
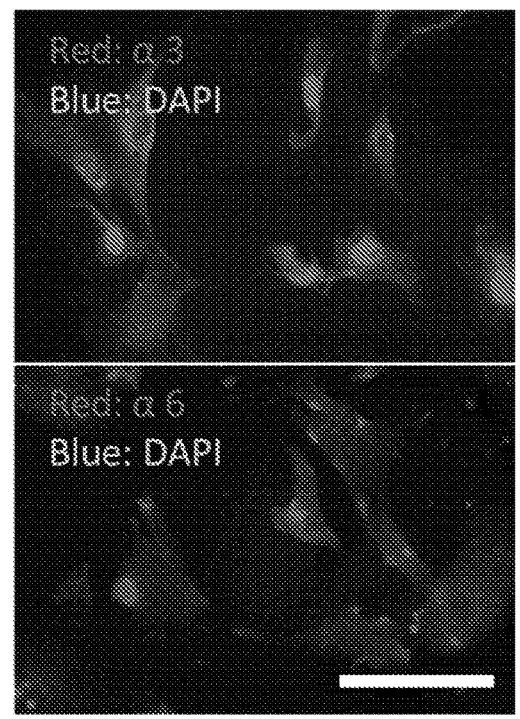
FIG. 4. The enhanced proliferation of the HDFs inside P-A5G81 is attenuated by anti-alpha3 and anti-alpha6 antibody treatments. (a) Integrin alpha3 and Integrin alpha6 staining of the HDFs. (b) HDFs proliferation response under different anti-integrin treatments. Statistical significance performed using one-way ANOVA with a Dunnet multiple comparison test (n≥10; *p<0.05; p<0.01; *p<0.001).
Figure 4:
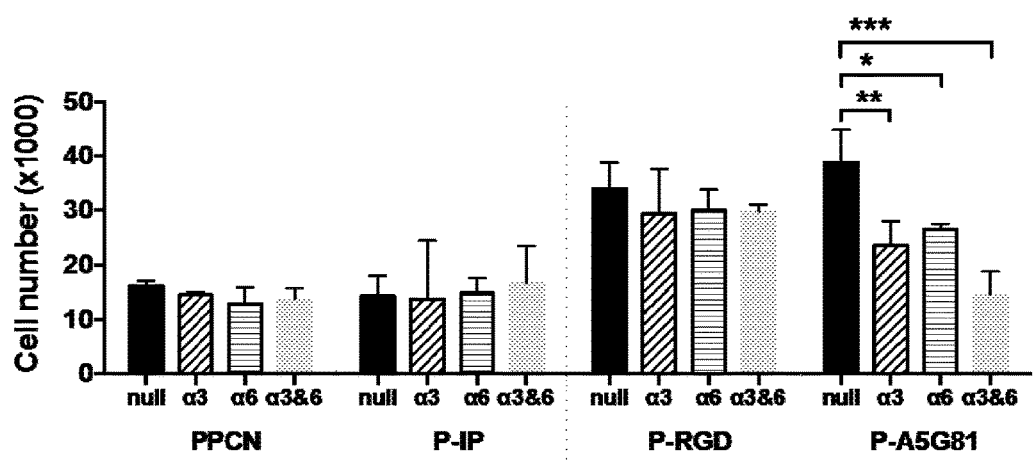

To further understand the cause of this enhanced proliferation behavior, A5G81 targeted binding integrin receptor $\alpha 3\beta 1$ and $\alpha 6\beta 1$ was closely studied. Immunostaining of the $\alpha 3$ and $\alpha 6$ indicated the presence of such integrin receptors on the cell membrane of HDFs (FIG. 4a). The integrin receptor blocking study was conducted using anti-$\alpha 3$ and anti-$\alpha 6$ antibodies (FIG. 4b). After 5 days in culture, the total DNA quantification indicates that partial blocking, only $\alpha 3$ or $\alpha 6$, only lead to a partial decrease of the cell proliferation, while completely blocking, both $\alpha 3$ and $\alpha 6$, cut the proliferation to the level which is close to the unfunctionalized PPCN scaffold. However, such proliferation blocking effect was only observed in the P-A5G81, in all three other groups PPCN, P-IP and P-RGD scaffold no significant difference was observed between each antibody treatment groups. These results indicated increased proliferation results from the specific integrin-cell-interaction between the HDFs and the A5G81 peptides; although the embodiments herein are not limited to any particular mechanism of action and an understanding of the mechanism of action is not necessary to practice such embodiments. Integrin $\alpha 3$ and $\alpha 6$ siRNA knock-down studies also confirmed such integrin-A5G81 associated proliferation behavior.

PPCN-A5G81 Gels Enhance In Vivo Wound Closure in a Diabetic Splinted Excisional Wound Model The in vivo performance of the PPCN-peptide dressing was evaluated using a db/db mouse splinted excisional wound model first reported by Galiano et al. (refs. 46, 47; incorporated by reference in their entireties). This model has two advantages that make it an accurate representation of the wound healing process in human diabetic patients. First, genetically induced hyperglycemia results in the characteristic diabetic complications in wound healing including reduced chemokine and growth factor release, impaired angiogenesis, prolonged inflammation and increased oxidative stress (refs. 47-49; incorporated by reference in their entireties). Another advantage stems from the use of splinting to prevent wound contraction, which is characteristic of rodent wound healing. As a result, the wound is allowed to heal through tissue regeneration, resembling the healing pattern of humans (refs. 46, 47, 50; incorporated by reference in its entirety). Skin contraction along the course of healing with and without splint failure confirms the validity of the db/db splinted wound model (ref 51; incorporated by reference in its entirety).

Figure 5:
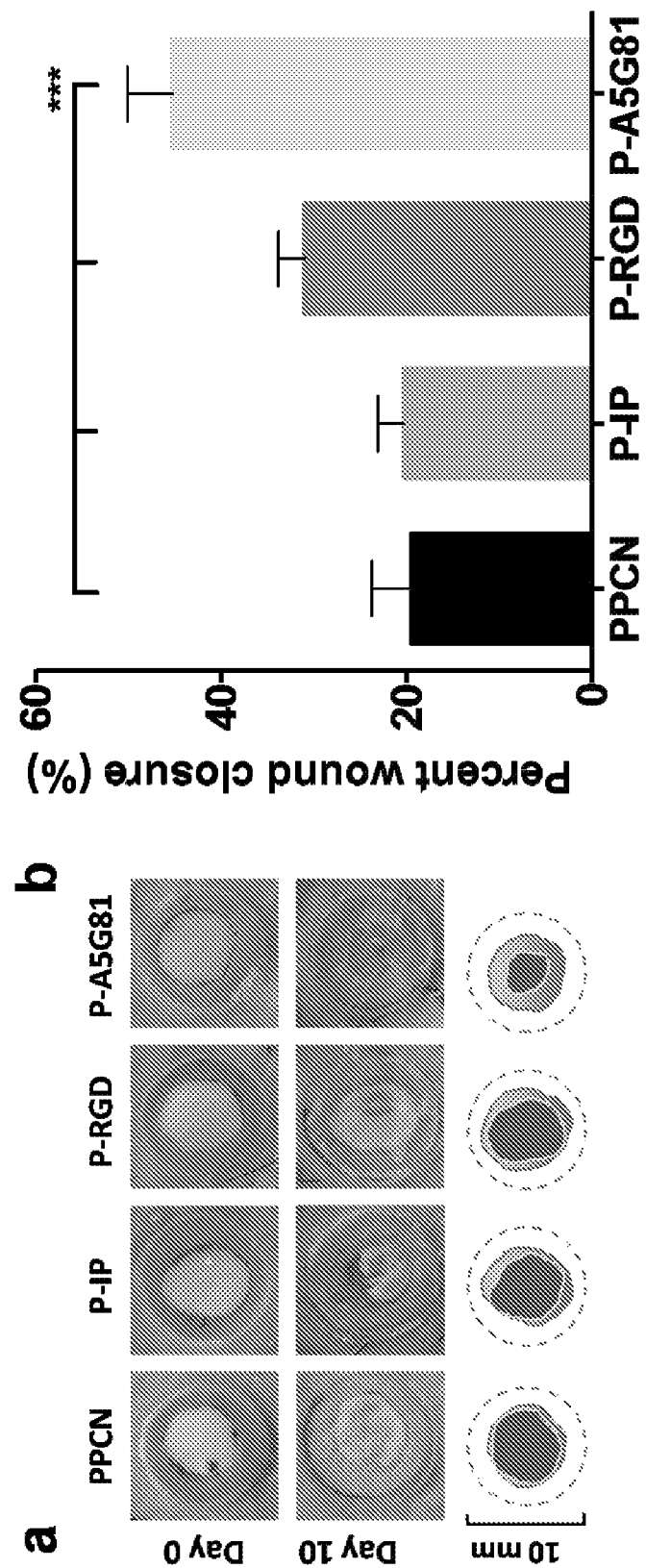
FIG. 5. P-A5G81 hydrogel promotes fast wound closure in the db/db excisional splinted wound models. (a) Digital images of the wound area for all four groups at day 10 after the initial wounding (top, middle). The overlay of the traces of wound-bad closure at day 0 and day 10. (b) Quantification of the wound closure at day 10 for all four groups. (c) 10-day healing curves for P-A5G81 vs. P-IP. (d) Summary of the complete wound closure time for all four groups. Statistical significance performed using one-way ANOVA with a Dunnet multiple comparison test (n≥5; ***p<0.01).
Figure 5:
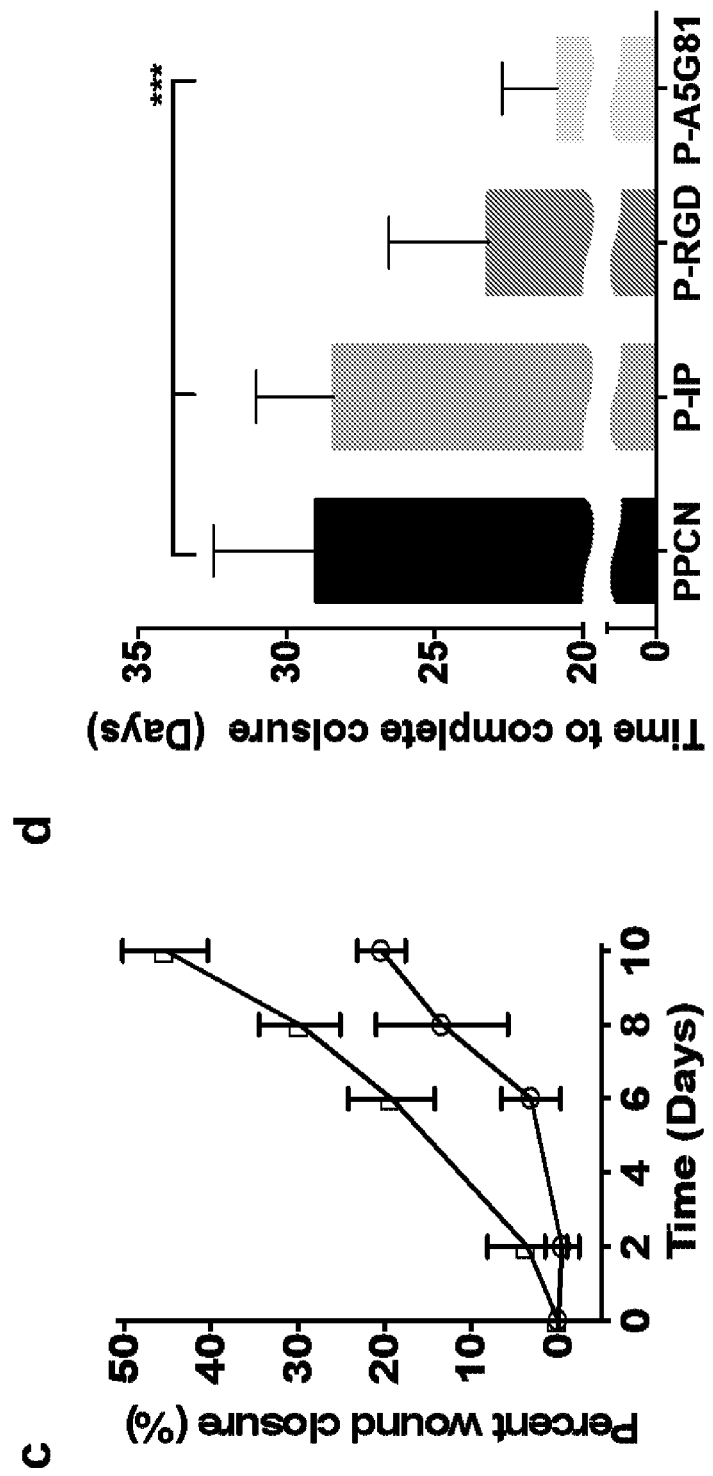

Incorporation of the A5G81 adhesion sequence into PPCN significantly enhanced the performance of the material in vivo. Application of the P-A5G81 hydrogel dressing on full thickness wounds in diabetic mice resulted in faster wound closure when compared to the PPCN and P-IP controls. A visual image of faster closing effect of P-A5G81 at day 10 is presented in FIG. 5a, which compares the open wound area with the initial wound size. Quantification of the percent wound closure at such time point showed averagely 45.3% relative to 31.1% of P-RGD, 20.4% of P-IP and 19.5% of PPCN (FIG. 5b). Pronounced differences between P-A5G81 and P-IP were seen even at early time points (FIG. 5c), due to the enhanced cell migration into the wound area. P-A5G81 treated wounds took 21 days to achieve the complete closure, which is one week faster than the PPCN and P-IP, 3 days faster than the P-RGD (FIG. 5d). This is the first description of A5G81 peptide in the context of wound healing, and results show that this peptide is particularly suitable for this application as it leads to significantly better healing rates than the commonly used RGD peptide.

PPCN-A5G81 Gel Promotes Granulation Tissue Formation and Reepithelialization

Figure 6:
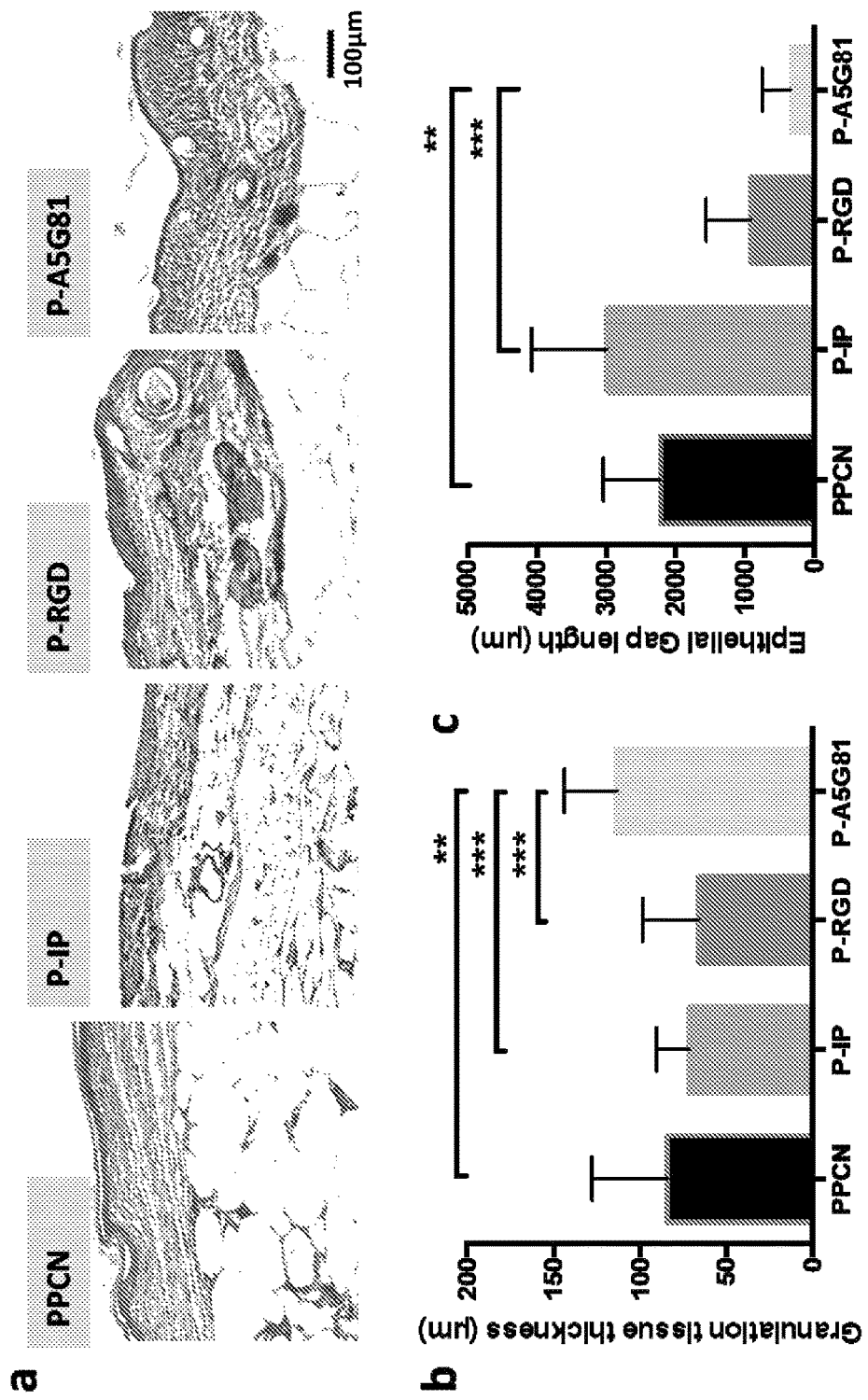
FIG. 6. P-A5G81 hydrogel allows faster tissue regeneration compared with the other groups in vivo. (a) H&E staining of tissue sections indicate the complete absorption of the hydrogel in all four groups 30 days post-surgery. The reepitheliazation was completed in all the groups expect P-IP (arrow indicates the uncovered area). (b) Thicker granulation tissue was found in the P-A5G81 treated wounds. (c) Quantification of the epithelial gap indicates minimum epithelial gap and maximum complete closure in the P-A5G81 group. (d) Immunofluorescence staining of the wound tissue sections indicates stratified expression of keratin-10 and Integrin 3 in the P-A5G81 treated wounds and minimum positive staining for macrophages (F4/80). Statistical significance performed using one-way ANOVA with a Dunnet multiple comparison test (n≥5; *p<0.05; p<0.01; *p<0.001).
Figure 6:
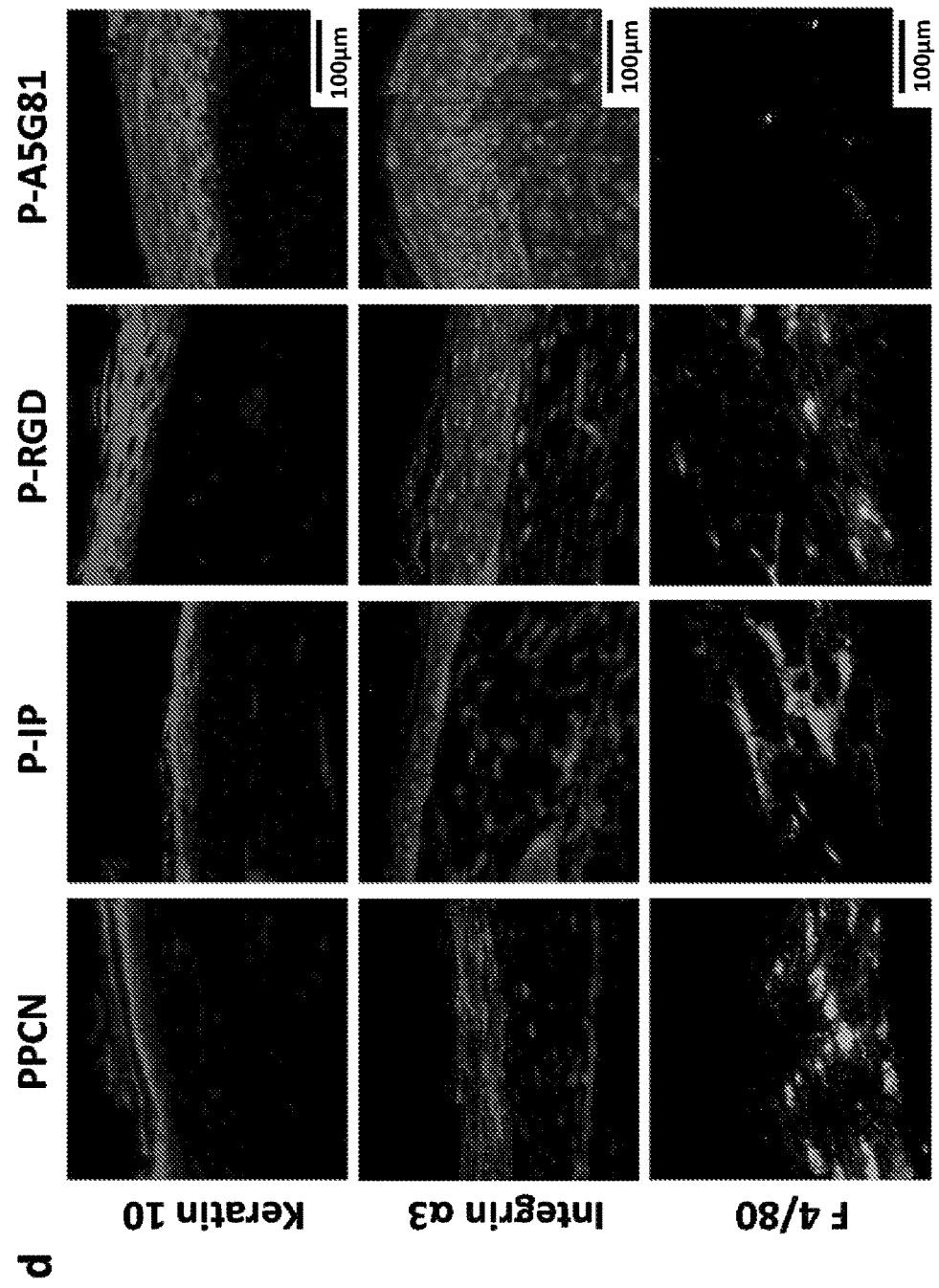

Wound closure and granulation tissue regeneration was accessed histologically through measurement of the epidermal gap and granulation tissue thickness. Histology of the regenerated wound tissue at day 30 (FIG. 6a) revealed close to complete reepithelialization (340 μm, around 5% relative to the initial wound size) in P-A5G81 treated wounds, whereas P-RGD, P-IP, and PPCN treated wounds remained 37%, 15% and 50% opening respectively at this time point (FIG. 6c). Granulation tissue was also significantly thicker by the time of closure of P-A5G81 treated wounds compared with PPCN, P-RGD, and P-IP groups (FIG. 6b). The gaps between the intact dermis at two wound edges have an average length of 5.45 mm (±0.32), which is very close to the initial wound diameter (6 mm). The quantification of the original wound size is evidence that wounds were primarily healed via tissue regeneration rather than of skin contraction. Additional studies comparing P-A5G81 and P-IP at day 10 revealed that the reduction in epidermal gap in P-A5G81 relative to the P-IP control wounds was first significantly observed by 10 days after two applications, by which time the P-A5G81-treated wounds had an epidermal gap of 25% of that of the P-IP control wounds (P<0.001). Within the same animal, while a thick granulation tissue was already prominent at the P-A5G81 treated side, the P-IP treated wound still remained open.

To evaluate tissue regeneration at the wound site, wound tissue from all four treatment groups were explanted, and stained for different cell markers, and analyzed by fluorescent microscopy to examine epithelial differentiation, integrin expression within the regenerated tissue and the foreign body response towards the hydrogel. All images were taken from the center point of the wounds. As shown by Keratin 10 staining, P-A5G81 treated wounds already had a multilayer epithelium structure by day 30, which closely resembles the reported health epidermis structure of the intact skin. While in the P-RGD groups, less prominent structure was observed, and in PPCN and P-IP groups, only a single un-continuous layer was stained barely covering the wound surface (FIG. 6d). P-A5G81 treated wounds were also populated by a significant amount of α3 positive cells, which further implied the role of A5G81 in promoting cell infiltration and proliferation during the healing process (FIG. 6d). Staining for macrophage cell marker F4/80 revealed minimum amount of macrophages within the P-A5G81 treated tissue, indicating a complete incorporation of the material by this time (FIG. 6d).

All publications and patents provided herein are incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

REFERENCES

The following references, some of which are cited above by number, are herein incorporated by reference in their entireties.
1. American Diabetes Association (2014) National Diabetes Statistics Report, 2014 Estimates of Diabetes and Its Burden in the Epidemiologic estimation methods. Natl Diabetes Stat Rep: 2009-2012.
2. Singh N, D G A, B A L (2005) Preventing foot ulcers in patients with diabetes. JAMA 293(2):217-228.
3. Moura L I F, Dias A M A, Carvalho E, de Sousa H C (2013) Recent advances on the development of wound dressings for diabetic foot ulcer treatment—A review. Acta Biomater 9(7):7093-7114.
4. Tran N Q, Joung Y K, Lih E, Park K D (2011) In Situ Forming and Rutin-Releasing Chitosan Hydrogels As Injectable Dressings for Dermal Wound Healing. Biomacromolecules 12(8):2872-2880.
5. Livant D L, et al. (2000) The PHSRN sequence induces extracellular matrix invasion and accelerates wound healing in obese diabetic mice. J Clin Invest 105(11):1537-1545.
6. Moura L I F, et al. (2014) Chitosan-based dressings loaded with neurotensin—an efficient strategy to improve early diabetic wound healing. Acta Biomater 10(2):843-857.
7. Banerjee P, Suguna L, Shanthi C (2014) Wound healing activity of a collagen-derived cryptic peptide. Amino Acids 47(2):317-328.
8. Del Gaudio P, et al. (2015) Evaluation of in situ injectable hydrogels as controlled release device for ANXA1 derived peptide in wound healing. Carbohydr Polym 115:629-635.
9. Rodgers K E, et al. (2003) Histological evaluation of the effects of angiotensin peptides on wound repair in diabetic mice. Exp Dermatol 12(6):784-90.
10. Strukova S M, et al. (2001) Immobilized thrombin receptor agonist peptide accelerates wound healing in mice. Clin Appl Thromb Hemost 7(4):325-329.
11. Waldeck H, Chung A S, Kao W J (2007) Interpenetrating polymer networks containing gelatin modified with PEGylated RGD and soluble KGF: Synthesis, characterization, and application in in vivo critical dermal wound. J Biomed Mater Res Part A 82A(4): 861-871.
12. Galiano R D, et al. (2004) Topical Vascular Endothelial Growth Factor Accelerates Diabetic Wound Healing through Increased Angiogenesis and by Mobilizing and Recruiting Bone Marrow-Derived Cells. Am J Pathol 164(6):1935-1947.
13. Li H, et al. (2008) Research of PDGF-BB Gel on the Wound Healing of Diabetic Rats and Its Pharmacodynamics. J Surg Res 145(1):41-48.
14. Gallagher K A, et al. (2007) Diabetic impairments in NO-mediated endothelial progenitor cell mobilization and homing are reversed by hyperoxia and SDF-1α. J Clin Invest 117(5):1249-1259.
15. Gibran N S, et al. (2002) Diminished Neuropeptide Levels Contribute to the Impaired Cutaneous Healing Response Associated with Diabetes Mellitus. J Surg Res 108(1):122-128.
16. Scott J R, et al. (2008) Topical Substance P Increases Inflammatory Cell Density in Genetically Diabetic Murine Wounds. Wound Repair Regen 16(4):529-533.
17. Hamed S, et al. (2010) Topical erythropoietin promotes wound repair in diabetic rats. J Invest Dermatol 130(1): 287-94.
18. Apikoglu-Rabus S, Izzettin F V, Turan P, Ercan F (2010) Effect of topical insulin on cutaneous wound healing in rats with or without acute diabetes. Clin Exp Dermatol 35(2):180-185.
19. Rizzi S C, Upton Z, Bott K, Dargaville T R (2010) Recent advances in dermal wound healing: biomedical device approaches. Expert Rev Med Devices 7(1):143-154.
20. van der Veen V C, van der Wal M B A, van Leeuwen M C E, Ulrich M M W, Middelkoop E (2010) Biological background of dermal substitutes. Burns 36(3):305-321.
21. Wong V W, Gurtner G C (2012) Tissue engineering for the management of chronic wounds: Current concepts and future perspectives. Exp Dermatol 21:729-734.
22. Mueller M M, Fusenig N E (2004) Friends or foes—bipolar effects of the tumour stroma in cancer. Nat Rev Cancer 4(11):839-849.
23. Schafer M, Werner S (2008) Cancer as an overhealing wound: an old hypothesis revisited. Nat Rev Mol Cell Biol 9(8):628-638.
24. Ziyadeh N, Fife D, Walker A M, Wilkinson G S, Seeger J D (2011) A matched cohort study of the risk of cancer in users of becaplermin. Adv Skin Wound Care 24(1):31-9.
25. Seet W T, et al. (2012) Shelf-life evaluation of bilayered human skin equivalent, MyDerm™. PLoS One 7(8): e40978.
26. Bellas E, Seiberg M, Garlick J, Kaplan D L (2012) In vitro 3D Full-Thickness Skin-Equivalent Tissue Model Using Silk and Collagen Biomaterials. Macromol Biosci 12(12):1627-1636.
27. Price R D, Das-Gupta V, Harris P a, Leigh I M, Naysaria H a (2004) The role of allogenic fibroblasts in an acute wound healing model. Plast Reconstr Surg 113:1719-1729.
28. Kolokol'chikova E G, Budkevich L I, Bobrovnikov A E, Badikova A K, Tumanov V P (2001) Morphological changes in burn wounds after transplantation of allogenic fibroblasts. Bull Exp Biol Med 131(1):89-93.
29. Yang J, van Lith R, Baler K, Hoshi R a, Ameer G a (2014) A thermoresponsive biodegradable polymer with intrinsic antioxidant properties. Biomacromolecules 15(11):3942-52.
30. Hozumi K, et al. (2009) Chain-Specific Heparin-Binding Sequences in the Laminin α Chain LG45 Modules. Biochemistry 48(23):5375-5381.
31. Katagiri F, et al. (2012) Screening of integrin-binding peptides from the laminin α4 and α5 chain G domain peptide library. Arch Biochem Biophys 521(1-2):32-42.
32. Nielsen P K, et al. (2000) Identification of a major heparin and cell binding site in the LG4 module of the laminin alpha 5 chain. J Biol Chem 275(19):14517-23.
33. Lin L, Kurpakus-Wheater M (2002) Laminin alpha5 chain adhesion and signaling in conjunctival epithelial cells. Invest Ophthalmol Vis Sci 43(8):2615-21.
34. Humphries J D, Byron A, Humphries M J (2006) INTEGRIN LIGANDS. J Cell Sci 119(Pt 19):3901-3903.
35. Rousselle P, et al. (2013) The syndecan binding sequence KKLRIKSKEK in laminin alpha3 LG4 domain promotes epidermal repair. Eur J Dermatol (November 2015). doi: 10.1684/ejd.2013.1974.
36. Frank D E, Carter W G (2004) Laminin 5 deposition regulates keratinocyte polarization and persistent migration. J Cell Sci 117(Pt 8):1351-1363.
37. Fujisaki H, Hattori S (2002) Keratinocyte apoptosis on type I collagen gel caused by lack of laminin 5/10/11 deposition and Akt signaling. Exp Cell Res 280(2):255-269.
38. Goldfinger L E, et al. (1999) The alpha3 laminin subunit, alpha6beta4 and alpha3beta1 integrin coordinately regulate wound healing in cultured epithelial cells and in the skin. J Cell Sci 112 (Pt 1:2615-2629.
39. Gonzales M, et al. (1999) A Cell Signal Pathway Involving Laminin-5, α3β1 Integrin, and Mitogen-activated Protein Kinase Can Regulate Epithelial Cell Proliferation. Mol Biol Cell 10 (February):259-270.
40. Xu J, Clark R A (1996) Extracellular matrix alters PDGF regulation of fibroblast integrins. J Cell Biol 132(1-2):239-49.
41. Nguyen B, Gil S, Carter W (2000) Deposition of laminin 5 by keratinocytes regulates integrin adhesion and signaling. J Biol Chem 275:31896-31907.
42. Maalej H, et al. (2014) Rhelogical, dermal wound healing and in vitro antioxidant properties of exopolysaccharide hydrogel from *Pseudomonas stutzeri* AS22. Colloids Surfaces B Biointerfaces 123:814-824.
43. Thirupathi Kumara Raja S, Thiruselvi T, Aravindhan R, Mandal A B, Gnanamani a. (2015) In vitro and in vivo assessments of a 3-(3,4-dihydroxyphenyl)-2-propenoic acid bioconjugated gelatin-based injectable hydrogel for biomedical applications. J Mater Chem B 00:1-15.
44. Gong C, et al. (2013) A biodegradable hydrogel system containing curcumin encapsulated in micelles for cutaneous wound healing. Biomaterials 34(27):6377-6387.
45. Li X, et al. (2012) In situ injectable nano-composite hydrogel composed of curcumin, N,O-carboxymethyl chitosan and oxidized alginate for wound healing application. Int J Pharm 437(1-2):110-119.
46. Galiano R D, Michaels V J, Dobryansky M, Levine J P, Gurtner G C (2004) Quantitative and reproducible murine model of excisional wound healing. Wound Repair Regen 12(4):485-492.
47. Michaels J, et al. (2007)<I>Db/Db</I> Mice Exhibit Severe Wound-Healing Impairments Compared With Other Murine Diabetic Strains in a Silicone-Splinted Excisional Wound Model. Wound Repair Regen 15(5):665-670.
48. Bagi Z, Koller A, Kaley G (2004) PPARgamma activation, by reducing oxidative stress, increases NO bioavailability in coronary arterioles of mice with Type 2 diabetes. Am J Physiol Heart Circ Physiol 286(2):H742-H748.
49. Werner S, Breeden M, Hubner G, Greenhalgh D G, Longaker M T (1994) Induction of Keratinocyte Growth Factor Expression Is reduced and Delayed During Wound Healing in the Genetically Diabetic Mouse. J Investig Dermatol 103(4):469-473.
50. Greenhalgh D G (2003) Wound healing and diabetes mellitus. Clin Plast Surg 30:37-45.
51. Park S A, et al. (2015) Importance of defining experimental conditions in a mouse excisional wound model. Wound Repair Regen 23(2):251-261.
52. Liu H, et al. (2014) A short peptide from frog skin accelerates diabetic wound healing. FEBS J 281(20):4633-4643.
53. Philp D, et al. (2003) Thymosin beta 4 and a synthetic peptide containing its actin-binding domain promote dermal wound repair in db/db diabetic mice and in aged mice. Wound Repair Regen 11(1):19-24.
54. Roy D C, Mooney N A, Raeman C H, Dalecki D, Hocking D C (2013) Fibronectin Matrix Mimetics Promote Full-Thickness Wound Repair in Diabetic Mice. Tissue Eng Part A 19(21-22):2517-2526.
55. Steed D L, et al. (1995) Promotion and acceleration of diabetic ulcer healing by arginine-glycine-aspartic acid (RGD) peptide matrix. RGD Study Group. Diabetes Care 18(1):39-46.
56. Murphy W L, Mercurius K O, Koide S (2004) Substrates for Cell Adhesion Prepared via Active Site-Directed Immobilization of a Protein Domain. (13):5048-5052.

The invention claimed is:

1. A composition comprising a poly(polyethyleneglycol citrate-co-N-isopropylacrylamide) (PPCN) carrier conjugated to an A5G81-based peptide that promotes cell adhesion, cell proliferation, and/or cell migration into the composition.

2. The composition of claim 1, wherein the A5G81-based peptide comprises at least 75% sequence similarity with SEQ ID NO: 1.

3. The composition of claim 1, wherein the peptide and/or PPCN further comprises reactive groups for conjugation.

4. The composition of claim 3, wherein the peptide comprises a terminal cysteine for conjugation to the PPCN via a N-benzoyl-4-(N-maleimido)-phenylhydrazide (BMPH) linker.

5. A wound dressing comprising a composition of claim 1.

6. A method of treating a wound comprising applying a wound dressing of claim 5 to the wound.

7. A method of treating a wound comprising applying a composition of claim 1 to the wound.

* * * * *

SEQUENCE LISTING

```
<160> NUMBER OF SEQ ID NOS: 34

<210> SEQ ID NO 1
<211> LENGTH: 12
<212> TYPE: PRT
<213> ORGANISM: Mus musculus

<400> SEQUENCE: 1

Ala Gly Gln Trp His Arg Val Ser Val Arg Trp Gly
1               5                   10
```

<210> SEQ ID NO 2
<211> LENGTH: 13
<212> TYPE: PRT
<213> ORGANISM: Artificial sequence
<220> FEATURE:
<223> OTHER INFORMATION: Modified version of A5G81

<400> SEQUENCE: 2

Ala Gly Gln Trp His Arg Val Ser Val Arg Trp Gly Cys
1               5                   10

<210> SEQ ID NO 3
<211> LENGTH: 12
<212> TYPE: PRT
<213> ORGANISM: Artificial sequence
<220> FEATURE:
<223> OTHER INFORMATION: Modified version of A5G81

<400> SEQUENCE: 3

Ala Gly Gln Trp His Arg Val Ser Val Arg Trp Cys
1               5                   10

<210> SEQ ID NO 4
<211> LENGTH: 11
<212> TYPE: PRT
<213> ORGANISM: Artificial sequence
<220> FEATURE:
<223> OTHER INFORMATION: Modified version of A5G81

<400> SEQUENCE: 4

Ala Gly Gln Trp His Arg Val Ser Val Arg Cys
1               5                   10

<210> SEQ ID NO 5
<211> LENGTH: 10
<212> TYPE: PRT
<213> ORGANISM: Artificial sequence
<220> FEATURE:
<223> OTHER INFORMATION: Modified version of A5G81

<400> SEQUENCE: 5

Ala Gly Gln Trp His Arg Val Ser Val Cys
1               5                   10

<210> SEQ ID NO 6
<211> LENGTH: 9
<212> TYPE: PRT
<213> ORGANISM: Artificial sequence
<220> FEATURE:
<223> OTHER INFORMATION: Modified version of A5G81

<400> SEQUENCE: 6

Ala Gly Gln Trp His Arg Val Ser Cys
1               5

<210> SEQ ID NO 7
<211> LENGTH: 8
<212> TYPE: PRT
<213> ORGANISM: Artificial sequence
<220> FEATURE:
<223> OTHER INFORMATION: Modified version of A5G81

<400> SEQUENCE: 7

Ala Gly Gln Trp His Arg Val Cys
1               5

<210> SEQ ID NO 8

```
<211> LENGTH: 7
<212> TYPE: PRT
<213> ORGANISM: Artificial sequence
<220> FEATURE:
<223> OTHER INFORMATION: Modified version of A5G81

<400> SEQUENCE: 8

Ala Gly Gln Trp His Arg Cys
1               5

<210> SEQ ID NO 9
<211> LENGTH: 6
<212> TYPE: PRT
<213> ORGANISM: Artificial sequence
<220> FEATURE:
<223> OTHER INFORMATION: Modified version of A5G81

<400> SEQUENCE: 9

Ala Gly Gln Trp His Cys
1               5

<210> SEQ ID NO 10
<211> LENGTH: 9
<212> TYPE: PRT
<213> ORGANISM: Artificial sequence
<220> FEATURE:
<223> OTHER INFORMATION: Modified version of A5G81

<400> SEQUENCE: 10

Gln Trp His Arg Val Ser Val Arg Cys
1               5

<210> SEQ ID NO 11
<211> LENGTH: 8
<212> TYPE: PRT
<213> ORGANISM: Artificial sequence
<220> FEATURE:
<223> OTHER INFORMATION: Modified version of A5G81

<400> SEQUENCE: 11

Gln Trp His Arg Val Ser Val Cys
1               5

<210> SEQ ID NO 12
<211> LENGTH: 8
<212> TYPE: PRT
<213> ORGANISM: Artificial sequence
<220> FEATURE:
<223> OTHER INFORMATION: Modified version of A5G81

<400> SEQUENCE: 12

Trp His Arg Val Ser Val Arg Cys
1               5

<210> SEQ ID NO 13
<211> LENGTH: 7
<212> TYPE: PRT
<213> ORGANISM: Artificial sequence
<220> FEATURE:
<223> OTHER INFORMATION: Modified version of A5G81

<400> SEQUENCE: 13

Trp His Arg Val Ser Val Cys
1               5

<210> SEQ ID NO 14
<211> LENGTH: 7
```

```
<212> TYPE: PRT
<213> ORGANISM: Artificial sequence
<220> FEATURE:
<223> OTHER INFORMATION: Modified version of A5G81

<400> SEQUENCE: 14

His Arg Val Ser Val Arg Cys
1               5

<210> SEQ ID NO 15
<211> LENGTH: 6
<212> TYPE: PRT
<213> ORGANISM: Artificial sequence
<220> FEATURE:
<223> OTHER INFORMATION: Modified version of A5G81

<400> SEQUENCE: 15

Ser Val Arg Trp Gly Cys
1               5

<210> SEQ ID NO 16
<211> LENGTH: 7
<212> TYPE: PRT
<213> ORGANISM: Artificial sequence
<220> FEATURE:
<223> OTHER INFORMATION: Modified version of A5G81

<400> SEQUENCE: 16

Val Ser Val Arg Trp Gly Cys
1               5

<210> SEQ ID NO 17
<211> LENGTH: 8
<212> TYPE: PRT
<213> ORGANISM: Artificial sequence
<220> FEATURE:
<223> OTHER INFORMATION: Modified version of A5G81

<400> SEQUENCE: 17

Arg Val Ser Val Arg Trp Gly Cys
1               5

<210> SEQ ID NO 18
<211> LENGTH: 9
<212> TYPE: PRT
<213> ORGANISM: Artificial sequence
<220> FEATURE:
<223> OTHER INFORMATION: Modified version of A5G81

<400> SEQUENCE: 18

His Arg Val Ser Val Arg Trp Gly Cys
1               5

<210> SEQ ID NO 19
<211> LENGTH: 10
<212> TYPE: PRT
<213> ORGANISM: Artificial sequence
<220> FEATURE:
<223> OTHER INFORMATION: Modified version of A5G81

<400> SEQUENCE: 19

Trp His Arg Val Ser Val Arg Trp Gly Cys
1               5                   10

<210> SEQ ID NO 20
<211> LENGTH: 11
<212> TYPE: PRT
```

```
<213> ORGANISM: Artificial sequence
<220> FEATURE:
<223> OTHER INFORMATION: Modified version of A5G81

<400> SEQUENCE: 20

Gln Trp His Arg Val Ser Val Arg Trp Gly Cys
1               5                   10

<210> SEQ ID NO 21
<211> LENGTH: 12
<212> TYPE: PRT
<213> ORGANISM: Artificial sequence
<220> FEATURE:
<223> OTHER INFORMATION: Modified version of A5G81

<400> SEQUENCE: 21

Gly Gln Trp His Arg Val Ser Val Arg Trp Gly Cys
1               5                   10

<210> SEQ ID NO 22
<211> LENGTH: 13
<212> TYPE: PRT
<213> ORGANISM: Artificial sequence
<220> FEATURE:
<223> OTHER INFORMATION: Modified version of A5G81

<400> SEQUENCE: 22

Ala Gly Gln Trp His Arg Val Ser Val Arg Trp Gly Cys
1               5                   10

<210> SEQ ID NO 23
<211> LENGTH: 13
<212> TYPE: PRT
<213> ORGANISM: Artificial sequence
<220> FEATURE:
<223> OTHER INFORMATION: Modified version of A5G81

<400> SEQUENCE: 23

Ala Ala Gln Trp His Arg Val Ser Val Arg Trp Gly Cys
1               5                   10

<210> SEQ ID NO 24
<211> LENGTH: 13
<212> TYPE: PRT
<213> ORGANISM: Artificial sequence
<220> FEATURE:
<223> OTHER INFORMATION: Modified version of A5G81

<400> SEQUENCE: 24

Ala Gly Ala Trp His Arg Val Ser Val Arg Trp Gly Cys
1               5                   10

<210> SEQ ID NO 25
<211> LENGTH: 13
<212> TYPE: PRT
<213> ORGANISM: Artificial sequence
<220> FEATURE:
<223> OTHER INFORMATION: Modified version of A5G81

<400> SEQUENCE: 25

Ala Gly Gln Ala His Arg Val Ser Val Arg Trp Gly Cys
1               5                   10

<210> SEQ ID NO 26
<211> LENGTH: 13
<212> TYPE: PRT
<213> ORGANISM: Artificial sequence
```

-continued

```
<220> FEATURE:
<223> OTHER INFORMATION: Modified version of A5G81

<400> SEQUENCE: 26

Ala Gly Gln Ala His Arg Val Ser Val Arg Trp Gly Cys
1               5                   10

<210> SEQ ID NO 27
<211> LENGTH: 13
<212> TYPE: PRT
<213> ORGANISM: Artificial sequence
<220> FEATURE:
<223> OTHER INFORMATION: Modified version of A5G81

<400> SEQUENCE: 27

Ala Gly Gln Trp Ala Arg Val Ser Val Arg Trp Gly Cys
1               5                   10

<210> SEQ ID NO 28
<211> LENGTH: 13
<212> TYPE: PRT
<213> ORGANISM: Artificial sequence
<220> FEATURE:
<223> OTHER INFORMATION: Modified version of A5G81

<400> SEQUENCE: 28

Ala Gly Gln Trp His Ala Val Ser Val Arg Trp Gly Cys
1               5                   10

<210> SEQ ID NO 29
<211> LENGTH: 13
<212> TYPE: PRT
<213> ORGANISM: Artificial sequence
<220> FEATURE:
<223> OTHER INFORMATION: Modified version of A5G81

<400> SEQUENCE: 29

Ala Gly Gln Trp His Arg Ala Ser Val Arg Trp Gly Cys
1               5                   10

<210> SEQ ID NO 30
<211> LENGTH: 13
<212> TYPE: PRT
<213> ORGANISM: Artificial sequence
<220> FEATURE:
<223> OTHER INFORMATION: Modified version of A5G81

<400> SEQUENCE: 30

Ala Gly Gln Trp His Arg Val Ala Val Arg Trp Gly Cys
1               5                   10

<210> SEQ ID NO 31
<211> LENGTH: 13
<212> TYPE: PRT
<213> ORGANISM: Artificial sequence
<220> FEATURE:
<223> OTHER INFORMATION: Modified version of A5G81

<400> SEQUENCE: 31

Ala Gly Gln Trp His Arg Val Ser Ala Arg Trp Gly Cys
1               5                   10

<210> SEQ ID NO 32
<211> LENGTH: 13
<212> TYPE: PRT
<213> ORGANISM: Artificial sequence
<220> FEATURE:
```

-continued

```
<223> OTHER INFORMATION: Modified version of A5G81

<400> SEQUENCE: 32

Ala Gly Gln Trp His Arg Val Ser Val Ala Trp Gly Cys
1               5                   10

<210> SEQ ID NO 33
<211> LENGTH: 13
<212> TYPE: PRT
<213> ORGANISM: Artificial sequence
<220> FEATURE:
<223> OTHER INFORMATION: Modified version of A5G81

<400> SEQUENCE: 33

Ala Gly Gln Trp His Arg Val Ser Val Arg Ala Gly Cys
1               5                   10

<210> SEQ ID NO 34
<211> LENGTH: 13
<212> TYPE: PRT
<213> ORGANISM: Artificial sequence
<220> FEATURE:
<223> OTHER INFORMATION: Modified version of A5G81

<400> SEQUENCE: 34

Ala Gly Gln Trp His Arg Val Ser Val Arg Trp Ala Cys
1               5                   10
```